United States Patent
Yao et al.

(10) Patent No.: US 11,155,559 B2
(45) Date of Patent: Oct. 26, 2021

(54) SULFONYL-SUBSTITUTED ISOQUINOLINES AS INHIBITORS OF RHO KINASE AND HERG POTASSIUM CHANNEL ACTIVITY

(71) Applicant: CHINA RESOURCES PHARMACEUTICAL HOLDINGS COMPANY LIMITED, Beijing (CN)

(72) Inventors: Yuanshan Yao, Shanghai (CN); Li Zhang, Shanghai (CN); Zhaoguo Chen, Shanghai (CN); Lele Zhao, Shanghai (CN); Lingyun Wu, Shanghai (CN); Shuhui Chen, Shanghai (CN)

(73) Assignee: CHINA RESOURCES PHARMACEUTICAL HOLDINGS COMPANY LIMITED, Beijing (CN)

( * ) Notice: Subject to any disclaimer, the term of this patent is extended or adjusted under 35 U.S.C. 154(b) by 0 days.

(21) Appl. No.: 16/631,417

(22) PCT Filed: Jul. 18, 2018

(86) PCT No.: PCT/CN2018/096134
§ 371 (c)(1),
(2) Date: Jan. 15, 2020

(87) PCT Pub. No.: WO2019/015608
PCT Pub. Date: Jan. 24, 2019

(65) Prior Publication Data
US 2020/0207772 A1 Jul. 2, 2020

(30) Foreign Application Priority Data

Jul. 19, 2017 (CN) .......................... 201710590957.X

(51) Int. Cl.
*A61K 31/472* (2006.01)
*C07D 217/00* (2006.01)
*C07D 487/04* (2006.01)

(52) U.S. Cl.
CPC .................................. *C07D 487/04* (2013.01)

(58) Field of Classification Search
CPC .............................. A61K 31/472; C07D 217/00
USPC ........................................... 514/307; 546/139
See application file for complete search history.

(56) References Cited

U.S. PATENT DOCUMENTS

2017/0037050 A1 2/2017 Wu et al.

FOREIGN PATENT DOCUMENTS

| CN | 105085525 A | 11/2015 |
|----|---|---|
| EP | 3138843 A1 | 3/2017 |
| JP | 2017-513919 A | 6/2017 |
| WO | WO-2004106325 A1 | 12/2004 |
| WO | WO-2015165341 A1 | 11/2015 |

OTHER PUBLICATIONS

International Search Report and Written Opinion of PCT/CN2018/096134 dated Oct. 17, 2018.
Jan. 11, 2021 Chinese Office Action issued in Chinese Patent Application No. 201880047583X.
Feb. 17, 2021 Extended European Search Report issued in Europe Patent Application No. 18834742.1.
Feb. 18, 2021 Japanese Office Action issued in Japanese Patent Application No. JP2020524668.
Mar. 12, 2021 Canadian Office Action issued in Canadian Patent Application No. CA 3,070,098.
May 28, 2021 Chinese Office Action issued in Chinese Patent Application No. 201880047583.X.
Aug. 2, 2021 Korean Notification of Reason for Refusal issued in Korean Patent Application No. 20207004711.

*Primary Examiner* — Douglas M Willis
(74) *Attorney, Agent, or Firm* — Harness, Dickey & Pierce, P.L.C.

(57) ABSTRACT

Disclosed are a class of isoquinoline compounds acting as RHO protein kinase inhibitors, and the use thereof in the preparation of a drug for treating diseases associated with RHO protein kinase. Particularly disclosed are compounds as shown in formula (I) and pharmaceutically acceptable salts thereof.

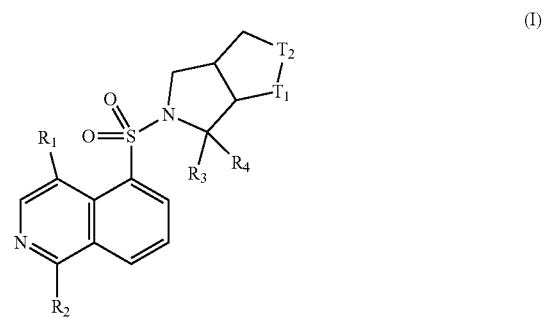

11 Claims, 1 Drawing Sheet

Figure 1:
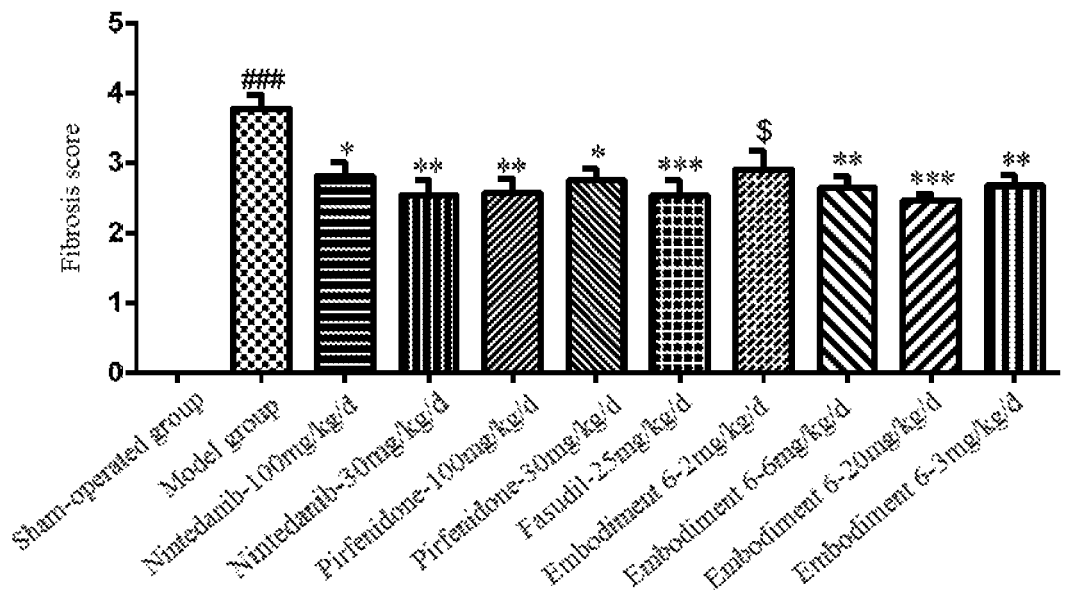

SULFONYL-SUBSTITUTED ISOQUINOLINES AS INHIBITORS OF RHO KINASE AND HERG POTASSIUM CHANNEL ACTIVITY

CROSS-REFERENCE TO RELATED APPLICATIONS

The present application is a 371 National Phase of International Application No. PCT/CN2018/096134, filed Jul. 18, 2018, which claims the benefit of Chinese Patent Application No. 201710590957.X, filed Jul. 19, 2017. The entire disclosures of the above applications are incorporated herein by reference.

FIELD

The present disclosure relates to a class of isoquinoline sulfonyl derivatives as RHO protein kinase inhibitors and pharmaceutical compositions thereof. Specifically, the present disclosure relates to a compound represented by formula (I) or a pharmaceutically acceptable salt thereof.

BACKGROUND

Fasudil is a novel drug with a wide range of pharmacological effects, it's a RHO kinase inhibitor that can expand blood vessels, reduce the tension of endothelial cells and improve the microcirculation of brain tissue by increasing the activity of myosin light chain phosphatase, which does not produce and aggravate the stealing of blood in the brain. And at the same time Fasudil can antagonize inflammatory factors, protect nerves against apoptosis, and promote nerve regeneration. Results show that Fasudil hydrochloride has a certain effect on promoting the recovery of neural function, reducing clinical symptoms and the rate of disability. Therefore, due to economic constraints at the grassroots level and the degree of awareness of the disease, ultra-early thrombolytic therapy cannot be achieved, but in order to reduce the further progress of the disease, it is important to rebuild local blood circulation within the treatment time window, while Fasudil hydrochloride has significant neuroprotective and therapeutic effects on ischemic cerebrovascular disease, it's worth of being used in clinic, especially at the grassroots level, to reduce the disability rate and improve the quality of life. Clinical use of nintedanib and pirfenidone have a relative good effect on pulmonary fibrosis.

The published patent WO2015/165341 has reported the compound represented by the following formula (Embodiment 38). As a ROCK kinase inhibitor, this compound has good enzyme activity, but its pharmacokinetic properties and hERG activity are not so ideal. The current patent reports a class of structurally modified analogous compounds that significantly improve this aspect of the property.

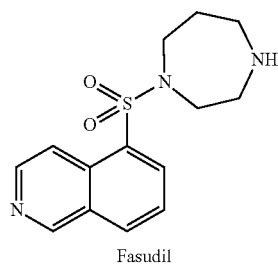

Fasudil

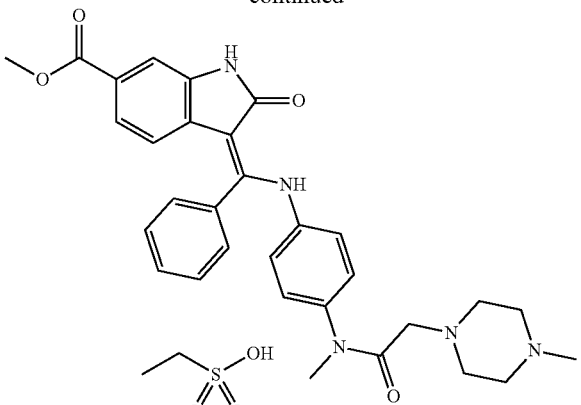

Nintedanib

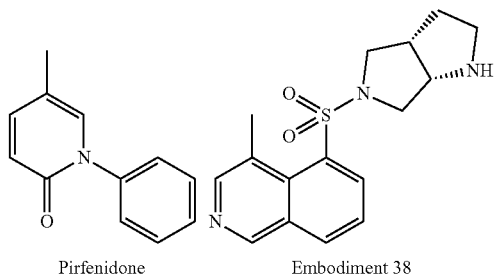

Pirfenidone     Embodiment 38

SUMMARY

The present disclosure aims to provide a compound represented by formula (I) and a pharmaceutical acceptable salt thereof or a tautomer thereof:

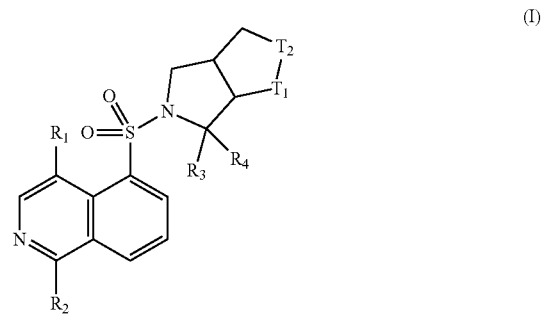

(I)

wherein,
$T_1$, $T_2$ are independently selected from: NH and $CH_2$;
$R_1$, $R_3$ are independently selected from H, F, Cl, Br, I, OH, $NH_2$, or $C_{1-3}$ alkyl, wherein the $C_{1-3}$ alkyl is optionally substituted by 1, 2 or 3 R;
$R_2$ is selected from H, F, Cl, Br, I, OH or $NH_2$;
$R_4$ is selected from $C_{1-3}$ alkyl which is optionally substituted by R, and the number of R is 1, 2 or 3;
alternatively, $R_3$ and $R_4$ are linked together to form a 3- to 6-membered ring which is optionally substituted by 1, 2 or 3 R;
each of R is selected from: F, Cl, Br, I, OH and $NH_2$.

In some embodiments of the present disclosure, the $R_1$, the $R_3$ are independently selected from H, F, Cl, Br, I, OH, $NH_2$ or $CH_3$.

In some embodiments of the present disclosure, the $R_4$ is selected from: $CH_3$.

In some embodiments of the present disclosure, the structural unit

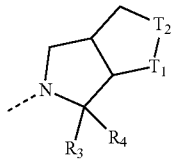

is selected from:

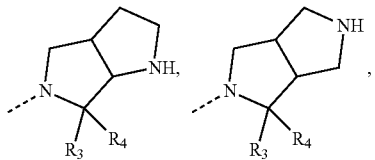

wherein $R_3$, $R_4$ are as defined in the present disclosure.

In some embodiments of the present disclosure, the structural unit

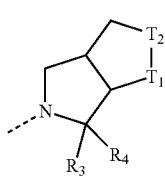

is selected from:

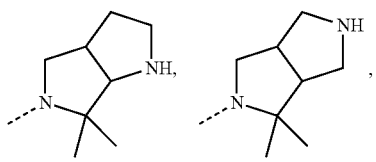

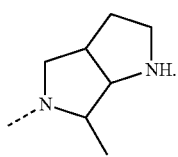

In some embodiments of the present disclosure, the $R_3$ and the $R_4$ are linked together to form a 3-membered ring which is optionally substituted by 1, 2 or 3 R, and R is as defined in the present disclosure.

In some embodiments of the present disclosure, the structural unit

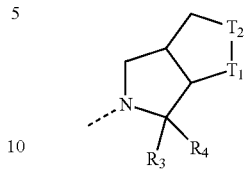

is selected from:

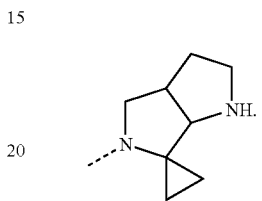

In some embodiments of the present disclosure, the $R_1$, the $R_3$ are independently selected from H, F, Cl, Br, I, OH, $NH_2$ and $CH_3$, the other variants are as defined above.

In some embodiments of the present disclosure, the $R_4$ is selected from: $CH_3$, the other variants are as defined above.

In some embodiments of the present disclosure, the structural unit

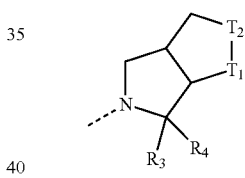

is selected from:

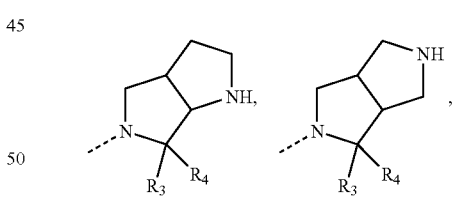

the other variants are as defined above.

In some embodiments of the present disclosure, the structural unit

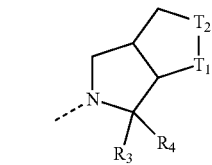

is selected from:

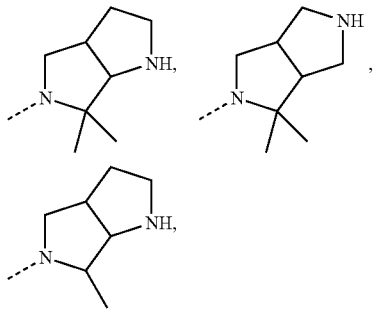

the other variants are as defined above.

In some embodiments of the present disclosure, the R₃ and the R₄ are linked together to form a 3-membered ring which is optionally substituted by 1, 2 or 3 R, and the other variants are as defined above.

In some embodiments of the present disclosure, the structural unit

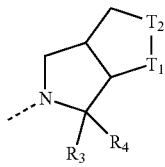

is selected from:

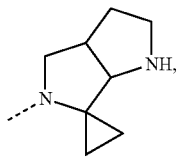

the other variants are as defined above.

In some embodiments of the present disclosure, the compound or the pharmaceutically acceptable salt thereof or the tautomer thereof is selected from:

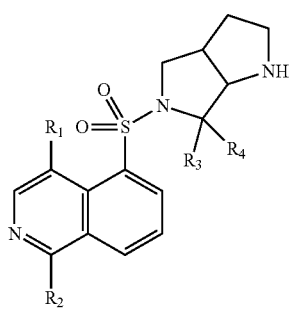

and (I-1)

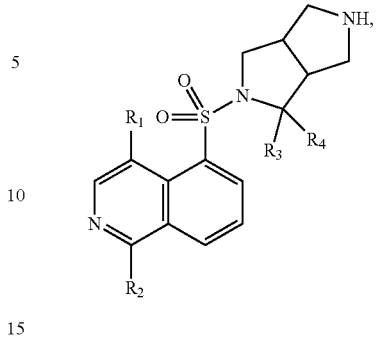

(I-2)

wherein, R¹ to R₄ are as defined above.

Some other embodiments of the present disclosure are arbitrary combinations the variants above.

The present disclosure further provides a compound, a pharmaceutically acceptable salt thereof or a tautomer thereof, which is selected from:

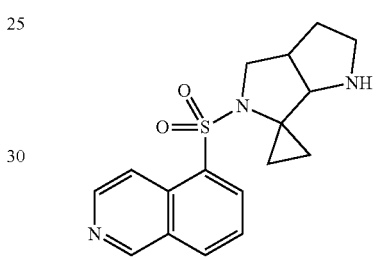

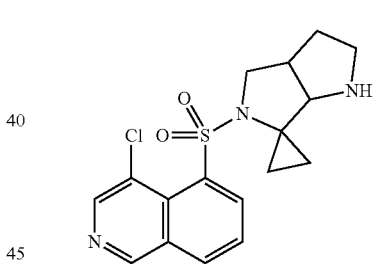

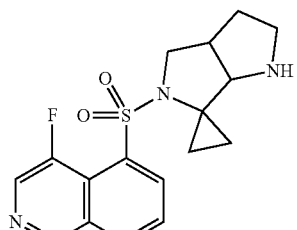

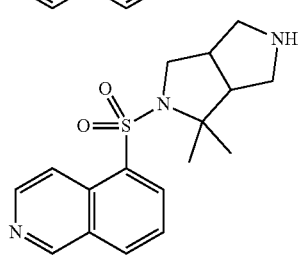

-continued

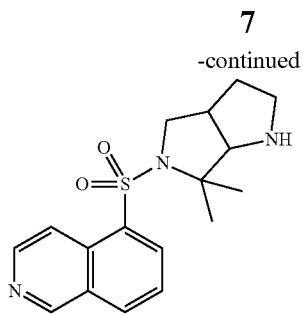

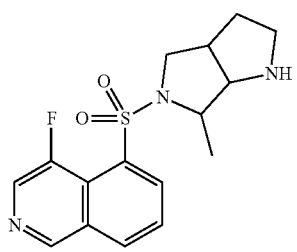

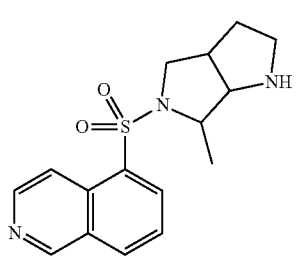

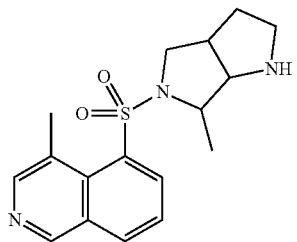

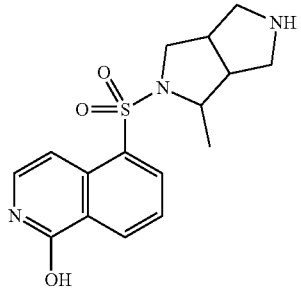

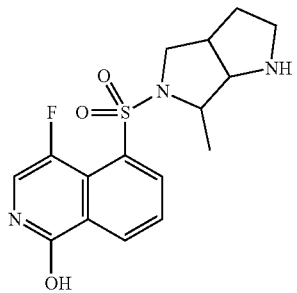

-continued

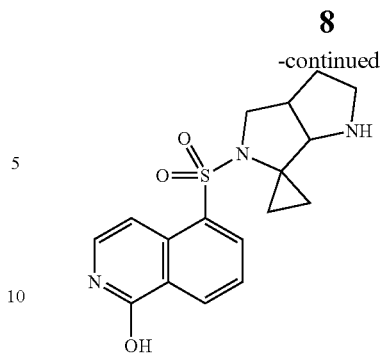

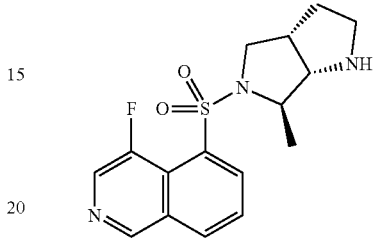

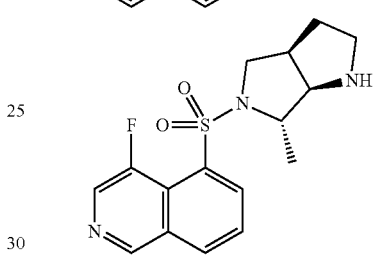

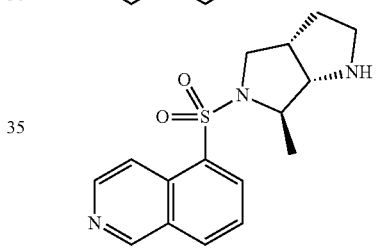

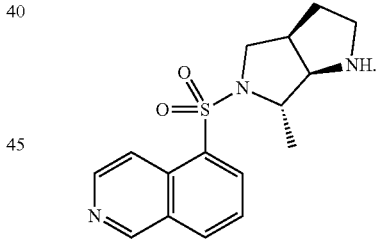

The present disclosure also provides a pharmaceutical composition comprising a therapeutically effective amount of the compound, the tautomer thereof or the pharmaceutically acceptable salt thereof as an active ingredient, and a pharmaceutically acceptable carrier.

The present disclosure also provides a use of the compound, the tautomer or the pharmaceutically acceptable salt thereof, or the composition in manufacturing a medicament for treating related disorders caused by vasoconstriction.

Unless otherwise indicated, the following terms when used in the descriptions and the claims of the present disclosure have the following meanings. A specific term or phrase should not be considered indefinite or unclear in the absence of a particular definition, but should be understood in the ordinary sense. When a trade name appears herein, it is intended to refer to its corresponding commodity or active ingredient thereof. The term "pharmaceutically acceptable"

is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium or similar salts. When the compound of the present disclosure contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like. Certain specific compounds of the present disclosure that contain both basic and acidic functional groups can be converted to any base or acid addition salt.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof. Some compounds of the present disclosure may exist in unsolvated or solvated forms, including hydrated forms. Generally speaking, the solvated form is equivalent to the unsolvated form, and both are included in the scope of the present disclosure.

Some compounds of the disclosure may have asymmetric carbon atoms (optical centers) or double bonds. Racemates, diastereomers, geometric isomers and individual isomers are included within the scope of the present disclosure.

Unless otherwise specified, the absolute configuration of a stereogenic center is represented by a wedged solid bond (╱) and a wedged dashed bond (╱⋯), A wave line (╱ᵕ) represents a wedged solid bond or a wedged dashed bond ( ╱ or ╱⋯ ), and ╱ ╱⋯ represent relative configuration of a solid center. When the compounds described herein contain olefinic double bonds or other centers of geometric asymmetry, unless otherwise specified, they include E, Z geometric isomers. Likewise, all tautomeric forms are included within the scope of the disclosure.

The compounds of the disclosure may exist in specific geometric or stereoisomeric forms. The present disclosure contemplates all such compounds, including cis and trans isomers, (−)- and (+)-enantiomers, (R)- and (S)-enantiomers, diastereomers isomers, (D)-isomers, (L)-isomers, and racemic and other mixtures thereof, such as enantiomers or diastereomeric enriched mixtures, all of which are within the scope of the disclosure. Additional asymmetric carbon atoms may be present in substituents such as alkyl. All these isomers and their mixtures are included within the scope of the present disclosure.

Optically active (R)- and (S)-isomer, or D and L isomer can be prepared using chiral synthesis or chiral reagents or other conventional techniques. If one kind of enantiomer of certain compound of the present disclosure is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (such as carbamate generated from amine).

The compounds of the present disclosure may contain atomic isotopes in unnatural proportions on one or more of the atoms constituting the compound. For example, the compound can be radiolabeled with a radioactive isotope, such as tritium ($^3$H), iodine-125 ($^{125}$I) or C-14 ($^{14}$C). Transformations of all isotopic compositions of the compounds of the disclosure, whether radioactive or not, are included within the scope of the disclosure.

The term "pharmaceutically acceptable carrier" refers to any agent or carrier medium which is capable of delivering an effective amount of the active substance of the present disclosure, does not interfere with the biological activity of the active substance and has no toxic side effect on the host or patient. The representative carrier includes water, oil, vegetable and mineral, cream base, lotion base, ointment base and the like. The base includes a suspending agent, a thickener, a penetration enhancer and the like. Their formulations are well known to the skilled in the cosmetic field or the topical pharmaceutical field.

"Optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted by a substituent, including deuterium and hydrogen variants, as long as the valence of the specific atom is normal and the substituted compound is stable. When the substituent is a keto group (i.e. =O), it means two hydrogen atoms are substituted. Positions on an aromatic ring cannot be substituted by a keto group. The term "optionally substituted" means an atom can be substituted by a substituent or not, unless otherwise specified, the species and number of the substituent may be arbitrary as long as being chemically achievable.

When any variable (such as R) occurs in the constitution or structure of the compound more than once, the definition of the variable at each occurrence is independent. Thus, for example, if a group is substituted by 0-2 R, the group can be optionally substituted by up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of the variable is a single bond, it means that the two groups linked by the single bond are connected directly. For example, when L in A-L-Z represents a single bond, the structure of A-L-Z is actually A-Z.

When a substituent is vacant, it means that the substituent does not exist. For example, when X is vacant in A-X, the structure of A-X is actually A. When a bond of a substituent can be cross-linked to two atoms on a ring, such substituent can be bonded to any atom on the ring. For example, the structural unit

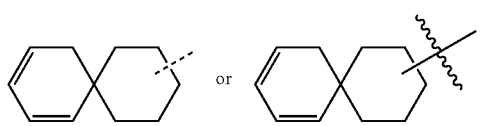

means that it can be substituted at any position on cyclohexyl or cyclohexadiene. When an enumerative substituent does not indicate by which atom it is attached to a compound included in the general chemical formula but not specifically mentioned, such substituent can be bonded by any of its atoms. For example, pyridyl as a substituent may be connected to a substituted group through any carbon atom on the pyridine ring. When the enumerative linking group does not indicate the direction for linking, the direction for linking is arbitrary, for example, the linking group L contained in

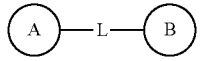

is -MW-, then -MW- can link ring A and ring B to form

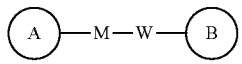

in the direction same as left-to-right reading order, and form

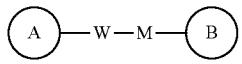

in the direction contrary to left-to-right reading order. Combinations of the linking groups, substituents and/or variants thereof are permissible only if such combinations result in stable compounds.

Unless otherwise specified, the term "ring" refers to a substituted or unsubstituted cycloalkyl, heterocycloalkyl, cycloalkenyl, heterocycloalkenyl, cycloalkynyl, heterocycloalkynyl, aryl or heteroaryl. The ring includes a single ring, a double ring, a spiral ring, a fused ring or a bridged ring. The number of the atom on the ring is usually defined as the member number of the ring, for example, a "5- to 7-membered ring" means that 5 to 7 atoms are arranged on a ring. Unless otherwise specified, the ring optionally contains 1 to 3 heteroatoms. Therefore, a "5- to 7-membered ring" includes, for example, phenyl, pyridinyl and piperidinyl; on the other hand, the term "5- to 7-membered heterocycloalkyl ring" includes pyridyl and piperidinyl, but excluding phenyl. The term "ring" also includes a ring system containing at least one ring, wherein each ring independently meets the above definition.

Unless otherwise specified, the term "hydrocarbyl" or its hyponyms (e.g., alkyl, alkenyl, alkynyl, and aryl, etc.), by itself or as part of another substituent, refers to a linear, branched chain or cyclic hydrocarbon radical or any combination thereof, they can be fully saturated (e.g., alkyl), mono- or polyunsaturated (e.g., alkenyl, alkynyl, and aryl), can be mono-, di- or poly-substituted, can be monovalent (e.g., methyl), divalent (e.g., methylene) or multivalent (e.g., methenyl), can also include a divalent or multivalent group, have a specified number of carbon atom (for example, $C_1$-$C_{12}$ indicates 1 to 12 carbon atoms, $C_{1-12}$ is selected from $C_1$, $C_2$, $C_3$, $C_4$, $C_5$, $C_6$, $C_7$, $C_8$, $C_9$, $C_{10}$, $C_{11}$ and $C_{12}$; $C_{3-12}$ is selected from $C_3$, $C_4$, $C_5$, $C_6$, $C_7$, $C_8$, $C_9$, $C_{10}$, $C_{11}$ and $C_{12}$). The term "hydrocarbyl" includes, but is not limited to, aliphatic hydrocarbyl and aromatic hydrocarbyl, the aliphatic hydrocarbyl includes linear and cyclic hydrocarbyl, specifically includes but not limited to alkyl, alkenyl, and alkynyl. The aromatic hydrocarbyl includes but is not limited to 6- to 12-membered aromatic hydrocarbyl such as phenyl, naphthyl and the like. In some embodiments, the term "hydrocarbyl" refers to a linear or branched group or a combination thereof which can be fully saturated, mono- or polyunsaturated, and can include a divalent or multivalent group. Examples of the saturated hydrocarbyl group include, but are not limited to, methyl, ethyl, n-propyl, isopropyl, n-butyl. Tert-butyl, isobutyl, sec-butyl, cyclohexyl, (cyclohexyl)methyl, cyclopropylmethyl, and the homolog or isomer of n-amyl, n-hexyl, n-heptyl, n-octyl and other atom groups. The unsaturated hydrocarbyl has one or more than one double or triple bonds. Examples of the unsaturated alkyl include but are not limited to, vinyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and more higher homologs and isomers.

Unless otherwise specified, the term "cyclohydrocarbyl", "heterocyclohydrocarbyl" or its hyponyms (such as aryl, heteroaryl, cycloalkyl, heterocycloalkyl, cycloalkenyl, heterocycloalkenyl, cycloalkynyl, heterocycloalkynyl, etc.) by itself or in combination with another term refers to cyclized "hydrocarbyl" or "heterohydrocarbyl". Furthermore, for heterohydrocarbyl or heterocyclohydrocarbyl (e.g., heteroalkyl, and heterocycloalkyl), one heteroatom can occupy the position where the heterocycle attaches to the remainder position of the molecule. Examples of the cycloalkyl include, but are not limited to, cyclopentyl, cyclohexyl, 1-cyclohexenyl, 3-cyclohexenyl, cycloheptyl and the like. Non-limiting examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydro-thiophen-2-yl, tetrahydro-thiophen-3-yl, 1-piperazinyl and 2-piperazinyl.

Unless otherwise specified, the term "alkyl" refers to a linear chain or branched saturated hydrocarbon group, can be mono-substituted (e.g., —$CH_2F$) or poly-substituted (e.g., —$CF_3$), can be monovalent (e.g., methyl), divalent (e.g., methylene) or multivalent (e.g., methenyl). Examples of alkyl include methyl (Me), ethyl (Et), propyl (such as n-propyl and isopropyl), butyl (such as n-butyl, isobutyl, s-butyl, tert-butyl), pentyl (such as n-pentyl, isopentyl, neopentyl) and the like.

Unless otherwise specified, cycloalkyl includes any stable cyclic or polycyclic hydrocarbyl, and any carbon atom is saturated, can be mono-substituted or poly-substituted, and can be monovalent, divalent or multivalent. Examples of cycloalkyl include, but are not limited to, cyclopropyl, norbornanyl, [2.2.2]bicyclooctane, [4.4.0]bicyclodecanyl and the like.

Unless otherwise specified, the term "halo" or "halogen" by itself or as part of another substituent refers to fluorine, chlorine, bromine or iodine atom. Furthermore, the term "haloalkyl" is meant to include monohaloalkyl and polyhaloalkyl. For example, the term "halo ($C_1$-$C_4$)alkyl" is meant to include, but not limited to, trifluoromethyl, 2,2,2-trifluoroethyl, 4-chlorobutyl, 3-bromopropyl and the like. Examples of haloalkyl include, but not limited to trifluoromethyl, trichloromethyl, pentafluoroethyl and pentachloroethyl.

The term "leaving group" refers to a functional group or atom which can be replaced by another functional group or atom through a substitution reaction (such as affinity substitution reaction). For example, representative leaving groups include triflate; chlorine, bromine and iodine; sulfonate group, such as mesylate, tosylate, p-bromobenzenesulfonate, p-toluenesulfonates and the like; acyloxy, such as acetoxy, trifluoroacetoxy and the like.

The term "protecting group" includes, but is not limited to "amino protecting group", "hydroxy protecting group" or "thio protecting group". The term "amino protecting group" refers to a protecting group suitable for blocking the side reaction on the nitrogen of an amino Representative amino protecting groups include, but are not limited to: formyl; acyl, such as alkanoyl (e.g. acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-bis-(4'-methoxyphenyl) methyl; silyl such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl such as methyl, ethyl and tert-butyl; acyl such as alkanoyl (e.g, acetyl); arylmethyl such as benzyl (Bn), p-methoxybenzyl (PMB), 9-fluorenylmethyl (Fm), and diphenylmethyl (benzhydryl, DPM); silyl such as trimethylsilyl (TMS) and tert-butyl dimethyl silyl (TBS) and the like.

The compound of the present disclosure can be prepared by a variety of synthetic methods well known to the skilled in the art, including the following enumerative embodiment, the embodiment formed by the following enumerative embodiment in combination with other chemical synthesis methods and the equivalent replacement well known to the skilled in the art. The preferred embodiment includes, but is not limited to the embodiment of the present disclosure.

The solvent used in the present disclosure is commercially available. The present disclosure employs the following abbreviations: aq stands for water; HATU stands for 0-(7-azabenzotriazol-1-yl)-N,N,N',N'-tetramethyluronium hexafluoro-phosphate; EDC stands for N-(3-dimethylaminopropyl)-N'-ethylcarbodiimide hydrochloride; m-CPBA stands for 3-chloroperoxybenzoic acid; eq stands for equivalent, equivalent; CDI stands for carbonyldiimidazole; DCM stands for dichloromethane; PE stands for petroleum ether; DIAD stands for diisopropyl azodicarboxylate; DMF stands for N,N-dimethylformamide; DMSO stands for dimethyl sulfoxide; EtOAc stands for ethyl acetate; EtOH stands for ethanol; MeOH for methanol; CBz stands for benzyloxycarbonyl, an amine protecting group; BOC stands for tert-butylcarbonyl is an amine protecting group; HOAc stands for acetic acid; $NaCNBH_3$ stands for sodium cyanoborohydride; r.t. stands for room temperature; O/N stands for overnight; THF stands for tetrahydrofuran; $Boc_2O$ stands for di-tert-butyldicarbonate; TFA stands for trifluoroacetic acid; DIPEA stands for diisopropylethylamine; $SOCl_2$ stands for thionyl chloride; $CS_2$ stands for carbon disulfide; TsOH stands for p-toluenesulfonic acid; NFSI stands for N-fluoro-N-(phenylsulfonyl)benzenesulfonamide; NCS stands for 1-chloropyrrolidine-2,5-dione; n-$Bu_4NF$ stands for tetrabutylammonium; iPrOH stands for 2-propanol; mp stands for melting point; LDA stands for diisopropylamino lithium; DIBAL-H stands for diisobutylaluminum hydride Compounds are named manually or by ChemDraw® software, the commercially available compounds use their vendor directory names.

The compound of the present disclosure has significant and unexpected protease inhibitory activity; in terms of PK, the half-life of the compound of the present disclosure is increased by about 3 times, and the clearance rate is significantly reduced, which proves that the present disclosure has superior properties over the prior art; in the meanwhile, compared with the existing technology, it has lower potential risk of hERG.

DRAWINGS

FIG. 1: Pulmonary fibrosis score
One-way ANOVA: ####p<0.001 vs. sham-operated group; *p<0.05 vs. model group;  p<0.01 vs. model group; *p<0.001 vs. model group; T-test: $p<0.05 vs. model group.

Figure 2:
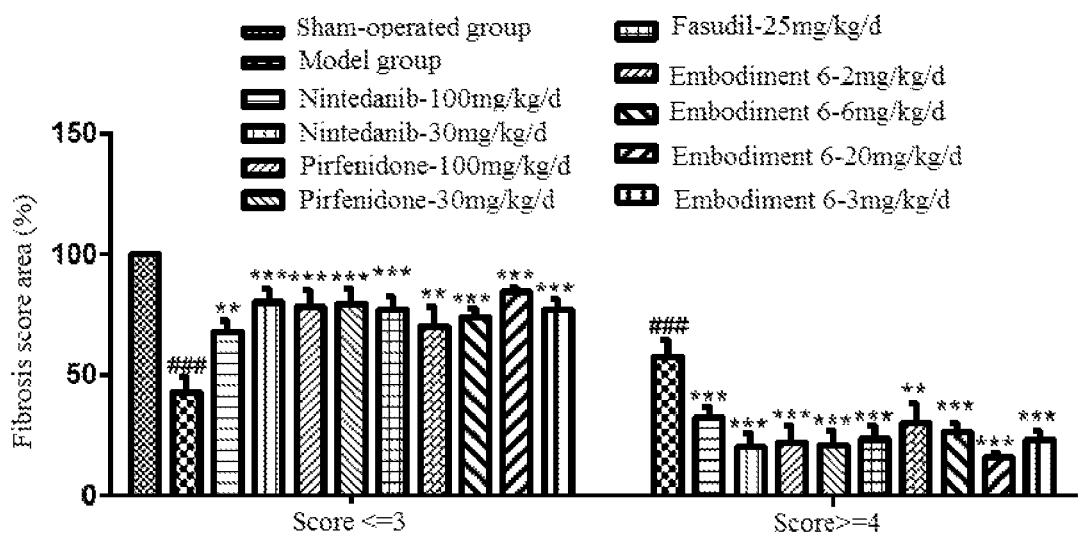

FIG. 2: Percentage of pulmonary fibrosis score
Two-way ANOVA: ####p<0.001 vs. sham operation group; *p<0.05 vs. model group; p<0.01 vs. model group; *p<0.001 vs. model group.

DETAILED DESCRIPTION

The following examples further illustrate the present invention, but the present disclosure is not limited thereto. The present disclosure has been described in detail in the text, and its specific embodiments have also been disclosed, for one skilled person in the art, it is obvious to modify and improve the embodiments of the present disclosure within the spirit and scope of the present invention.

Embodiment 1

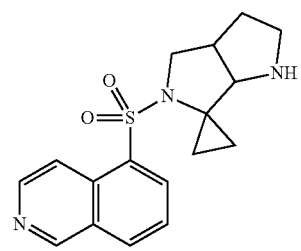

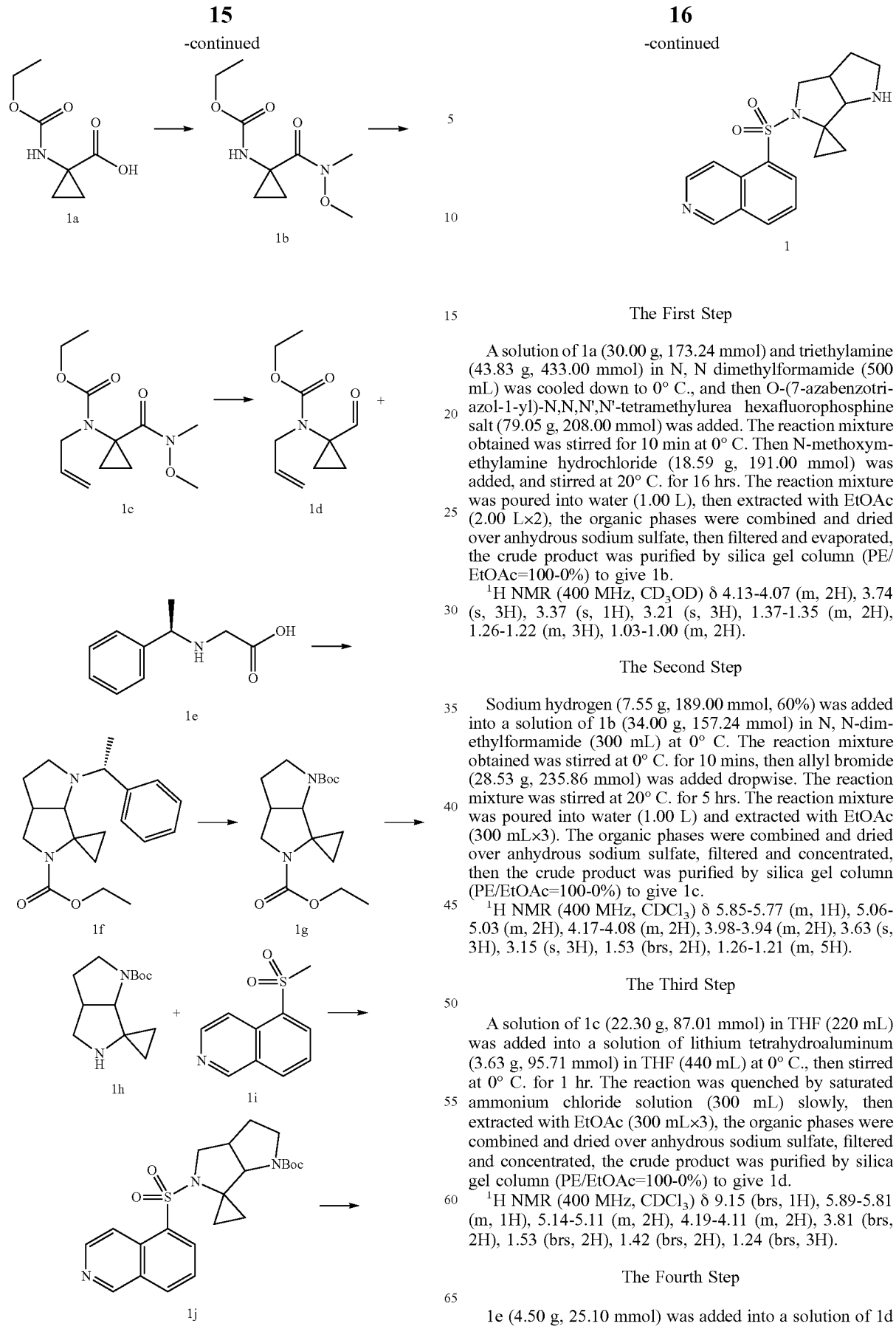

The First Step

A solution of 1a (30.00 g, 173.24 mmol) and triethylamine (43.83 g, 433.00 mmol) in N, N dimethylformamide (500 mL) was cooled down to 0° C., and then O-(7-azabenzotriazol-1-yl)-N,N,N',N'-tetramethylurea hexafluorophosphine salt (79.05 g, 208.00 mmol) was added. The reaction mixture obtained was stirred for 10 min at 0° C. Then N-methoxymethylamine hydrochloride (18.59 g, 191.00 mmol) was added, and stirred at 20° C. for 16 hrs. The reaction mixture was poured into water (1.00 L), then extracted with EtOAc (2.00 L×2), the organic phases were combined and dried over anhydrous sodium sulfate, then filtered and evaporated, the crude product was purified by silica gel column (PE/EtOAc=100-0%) to give 1b.

$^1$H NMR (400 MHz, CD$_3$OD) δ 4.13-4.07 (m, 2H), 3.74 (s, 3H), 3.37 (s, 1H), 3.21 (s, 3H), 1.37-1.35 (m, 2H), 1.26-1.22 (m, 3H), 1.03-1.00 (m, 2H).

The Second Step

Sodium hydrogen (7.55 g, 189.00 mmol, 60%) was added into a solution of 1b (34.00 g, 157.24 mmol) in N, N-dimethylformamide (300 mL) at 0° C. The reaction mixture obtained was stirred at 0° C. for 10 mins, then allyl bromide (28.53 g, 235.86 mmol) was added dropwise. The reaction mixture was stirred at 20° C. for 5 hrs. The reaction mixture was poured into water (1.00 L) and extracted with EtOAc (300 mL×3). The organic phases were combined and dried over anhydrous sodium sulfate, filtered and concentrated, then the crude product was purified by silica gel column (PE/EtOAc=100-0%) to give 1c.

$^1$H NMR (400 MHz, CDCl$_3$) δ 5.85-5.77 (m, 1H), 5.06-5.03 (m, 2H), 4.17-4.08 (m, 2H), 3.98-3.94 (m, 2H), 3.63 (s, 3H), 3.15 (s, 3H), 1.53 (brs, 2H), 1.26-1.21 (m, 5H).

The Third Step

A solution of 1c (22.30 g, 87.01 mmol) in THF (220 mL) was added into a solution of lithium tetrahydroaluminum (3.63 g, 95.71 mmol) in THF (440 mL) at 0° C., then stirred at 0° C. for 1 hr. The reaction was quenched by saturated ammonium chloride solution (300 mL) slowly, then extracted with EtOAc (300 mL×3), the organic phases were combined and dried over anhydrous sodium sulfate, filtered and concentrated, the crude product was purified by silica gel column (PE/EtOAc=100-0%) to give 1d.

$^1$H NMR (400 MHz, CDCl$_3$) δ 9.15 (brs, 1H), 5.89-5.81 (m, 1H), 5.14-5.11 (m, 2H), 4.19-4.11 (m, 2H), 3.81 (brs, 2H), 1.53 (brs, 2H), 1.42 (brs, 2H), 1.24 (brs, 3H).

The Fourth Step 1e (4.50 g, 25.10 mmol) was added into a solution of 1d (4.50 g, 22.82 mmol) in toluene (45 mL), then stirred for 72 hrs at 130° C. The reaction was quenched by 1N diluted hydrochloric acid (150 mL), and washed with EtOAc (50 mL×2). The pH of the remaining aqueous phase was adjusted to 12 with sodium hydroxide, and then extracted with the mixture of dichloromethane/methane=10:1 (100 mL×3), the organic phases were combined, and dried over anhydrous sodium sulfate, filtered and concentrated, the crude product was purified by silica gel column (PE/EtOAc=100-0%) to give 1f.

The Fifth Step

Wet palladium on carbon (1.20 g, 10%) was added into a solution of if (4.30 g, 13.68 mmol) and BOC$_2$O (4.48 g, 20.52 mmol) in methanol (100 mL). The reaction mixture obtained was stirred for 20 hrs at 50° C. under 50 psi hydrogen atmosphere, then the reaction mixture was filtered and concentrated, the crude product was purified by silica gel column (PE/EtOAc=100-0%) to give 1g.

The Sixth Step

Potassium hydroxide (22.24 g, 396.30 mmol) was added into a solution of 1g (4.10 g, 13.21 mmol) in ethanol (120 mL) and water (30 mL), the reaction mixture was stirred at 95° C. for 40 hrs. The reaction mixture was concentrated to eliminate ethanol, then extracted with dichloromethane (150 mL×5), the organic phase was dried over anhydrous sodium sulfate, filtered and concentrated, the crude product was purified by silica gel column (PE/EtOAc=100-0%) to give 1h.

$^1$H NMR (400 MHz, CDCl$_3$) δ 4.13-4.08 (m, 1H), 3.75-3.58 (m, 1H), 3.34-3.29 (m, 1H), 3.11-3.06 (m, 2H), 2.73-2.69 (m, 1H), 2.00-1.95 (m, 2H), 1.70-1.67 (m, 1H), 1.49-1.44 (m, 10H), 0.66-0.59 (m, 2H).

The Seventh Step

Triethylamine (170 mg, 1.68 mmol) was added dropwise into a solution of the compound 1h (200 mg, 0.84 mmol) and the compound 1i (287 mg, 1.26 mmol) in dichloromethane (10 mL). The reaction mixture obtained was reacted at 15° C. for 5 hrs. After completion of the reaction, the dichloromethane was eliminated directly, the crude product obtained was purified by preparative thin layer plate (EtOAc) to give the compound 1j.

$^1$H NMR (400 MHz, CDCl$_3$) δ 9.36-9.34 (m, 1H), 8.71-8.69 (m, 1H), 8.48-8.47 (m, 2H), 8.25-8.20 (m, 1H), 7.74-7.70 (m, 1H), 4.15-3.96 (m, 2H), 3.73-3.25 (m, 4H), 1.84-1.62 (m, 1H), 1.60 (brs, 3H), 1.38 (s, 9H), 1.26-0.68 (m, 2H).

The Eighth Step

At 20° C., HCl/EtOAc (4 mL, 4 M) was added into a solution of the compound 1j (130 mg, 0.30 mmol) in EtOAc (1 mL). The reaction mixture obtained was stirred at the same temperature for 2 hrs. After completion of the reaction, the mixture was filtered and dried to give the compound 1.

MS-ESI calculated value [M+H]$^+$ 330, measured value 330.

$^1$H NMR (400 MHz, D$_2$O) δ 9.75 (s, 1H), 8.81-8.65 (m, 4H), 8.08 (t, J=8.0 Hz, 1H), 4.10-4.07 (m, 1H), 3.93-3.91 (m, 1H), 3.79-3.74 (m, 1H), 3.51-3.48 (m, 1H), 3.42-3.25 (m, 2H), 2.41-2.39 (m, 1H), 2.03-2.02 (m, 1H), 1.39-1.36 (m, 1H), 1.14-1.12 (m, 1H), 0.81-0.78 (m, 1H), 0.54-0.53 (m, 1H).

Embodiment 2

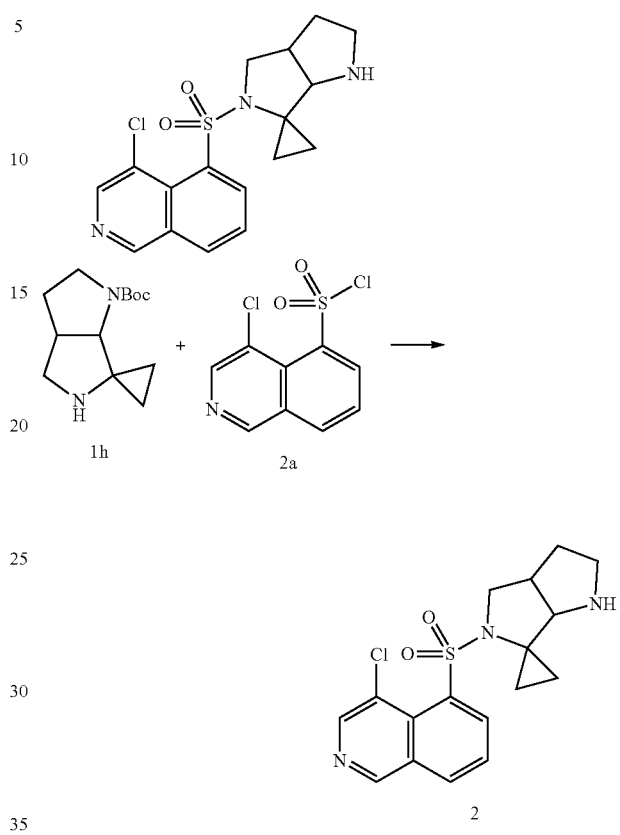

The First Step

The compound 2 was obtained from the compound 1h and the compound 2a using the synthesis method of the compound 1.

MS-ESI calculated value [M+H]$^+$ 364, measured value 364.

$^1$H NMR (400 MHz, D$_2$O) δ 9.30 (s, 1H), 8.67 (s, 1H), 8.62 (d, J=7.6 Hz, 1H), 8.46 (d, J=8.4 Hz, 1H), 7.86 (t, J=8.0 Hz, 1H), 4.05-3.94 (m, 2H), 3.82-3.77 (m, 1H), 3.57-3.55 (m, 1H), 3.38-3.22 (m, 2H), 2.42-2.39 (m, 1H), 2.08-2.04 (m, 1H), 1.06-0.79 (m, 4H).

Embodiment 3

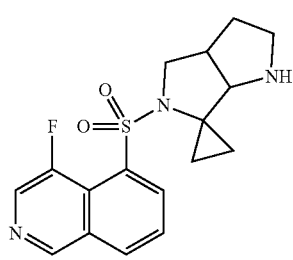

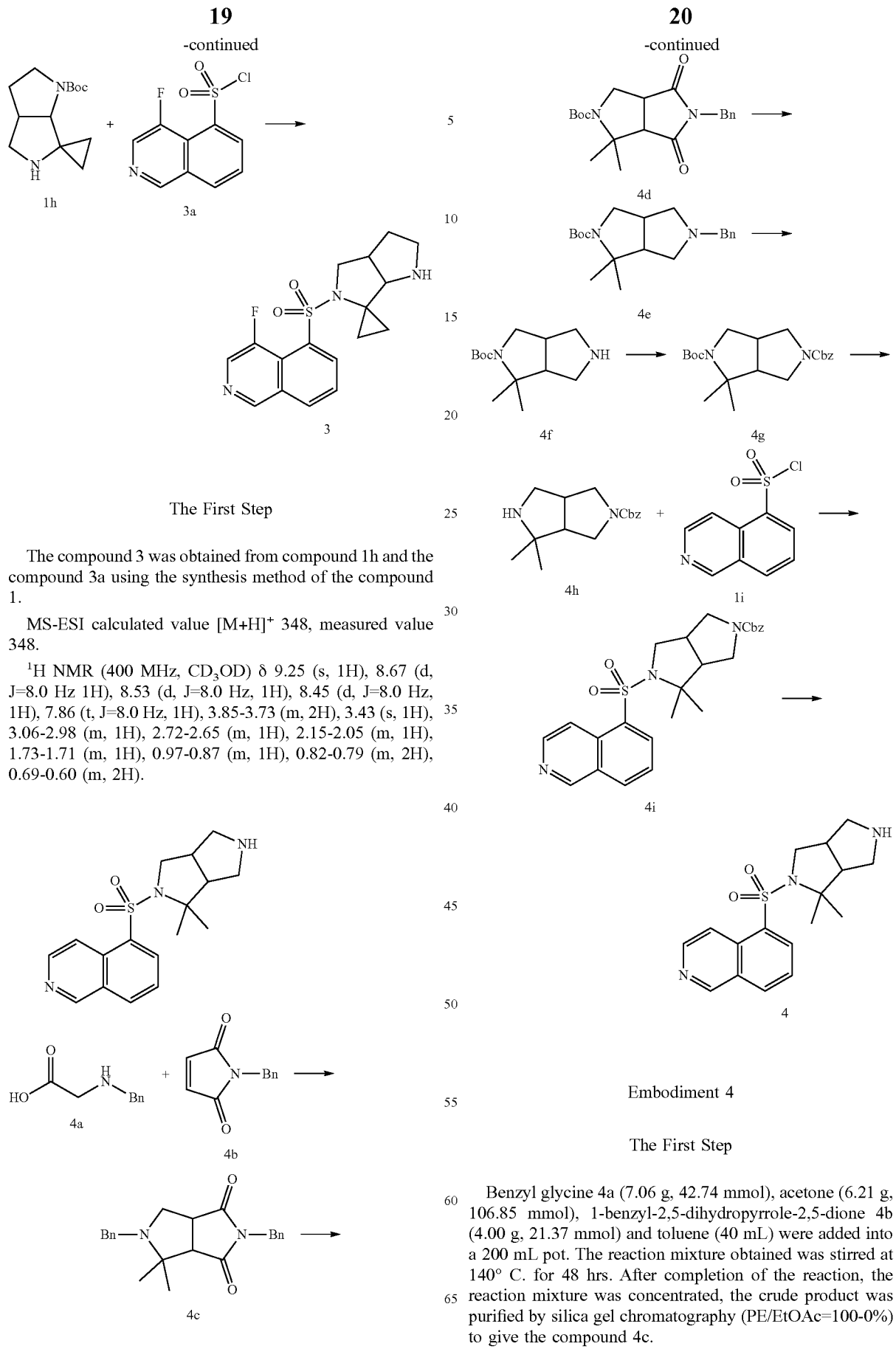

The First Step

The compound 3 was obtained from compound 1h and the compound 3a using the synthesis method of the compound 1.

MS-ESI calculated value [M+H]$^+$ 348, measured value 348.

$^1$H NMR (400 MHz, CD$_3$OD) δ 9.25 (s, 1H), 8.67 (d, J=8.0 Hz 1H), 8.53 (d, J=8.0 Hz, 1H), 8.45 (d, J=8.0 Hz, 1H), 7.86 (t, J=8.0 Hz, 1H), 3.85-3.73 (m, 2H), 3.43 (s, 1H), 3.06-2.98 (m, 1H), 2.72-2.65 (m, 1H), 2.15-2.05 (m, 1H), 1.73-1.71 (m, 1H), 0.97-0.87 (m, 1H), 0.82-0.79 (m, 2H), 0.69-0.60 (m, 2H).

Embodiment 4

The First Step

Benzyl glycine 4a (7.06 g, 42.74 mmol), acetone (6.21 g, 106.85 mmol), 1-benzyl-2,5-dihydropyrrole-2,5-dione 4b (4.00 g, 21.37 mmol) and toluene (40 mL) were added into a 200 mL pot. The reaction mixture obtained was stirred at 140° C. for 48 hrs. After completion of the reaction, the reaction mixture was concentrated, the crude product was purified by silica gel chromatography (PE/EtOAc=100-0%) to give the compound 4c.

¹H NMR (400 MHz, CDCl₃) δ 7.40-7.32 (m, 10H), 4.77-4.72 (t, J=5.2, 2H), 3.96-3.74 (m, 3H), 2.90-2.66 (m, 3H), 2.31 (s, 3H), 1.60 (s, 3H).

The Second Step

The compound 4c (5.28 g, 15.15 mmol) and 350 mL methanol was added into a 1000 mL hydrogenated bottle, under the protection of nitrogen, wet palladium on carbon (2.00 g, purity 10%) and Boc₂O (6.61 g, 30.30 mmol) were added, then the suspension was replaced with hydrogen for 3 times. The mixture obtained was stirred under hydrogen atmosphere (50 psi) at 50° C. for 16 hrs. After completion of the reaction, the reaction mixture was filtered, concentrated, the crude product was purified by silica gel chromatography (PE/EtOAc=100-0%) to give the compound 4d.

¹H NMR (400 MHz, CDCl₃) δ 7.23-7.20 (m, 5H), 4.57 (s, 2H), 2.93-2.83 (m, 4H), 1.41-1.36 (m, 15H).

The Third Step

The compound 4d (300 mg, 0.84 mmol) and 7 mL THF was added into a 50 mL three-neck round bottom flask, under the protection of nitrogen, borane-THF (1 M, 3.4 mL) was then added dropwise at 0° C., the reaction mixture obtained was stirred at 50° C. for 2.5 hrs. After completion of the reaction, the temperature was cooled to 0° C., methanol (10 mL) was added slowly to quench the reaction, then the reaction mixture was concentrated. Preparative thin layer chromatography was used for purification (PE/EtOAc=2:1) to give the compound 4e.

MS-ESI calculated value [M+H]⁺ 331, measured value 331.

¹H NMR (400 MHz, CDCl₃) δ 7.32-7.26 (m, 5H), 3.62 (s, 2H), 3.25 (s, 1H), 2.98-2.95 (m, 1H), 2.72-2.66 (m, 2H), 2.51-2.44 (m, 2H), 2.32-2.29 (m, 1H), 2.11 (m, 1H), 1.46-1.34 (m, 15H).

The Fourth Step

The compound 4e (100 mg, 0.30 mmol) and 5 mL methanol were added into a 50 mL hydrogenated bottle, under the protection of nitrogen, wet palladium on carbon (100 mg, purity 10%) was added, the suspension was replaced with nitrogen and hydrogen for 3 times sequentially. Then the mixed solution was stirred under hydrogen atmosphere (50 psi) at 50° C. for 12 hrs. After completion of the reaction, the reaction mixture was filtered and concentrated to give the compound 4f, which was used directly in the next step.

MS-ESI calculated value [M+H]⁺ 241, measured value 241.

The Fifth Step

The compound 4f (72 mg, the crude product obtained in previous step), N,N-diisopropylethylamine (77 mg, 0.60 mmol) and 1 mL dichloromethane were added into a 50 mL round bottom flask, benzyl chloroformate (77 mg, 0.45 mmol) was added dropwise slowly at 0° C. and under the protection of nitrogen. The reaction mixture was stirred at 25° C. for 3 hrs. After completion of the reaction, the reaction mixture was washed with N, N, N-trimethylethylenediamine (2 mL, 10%), then extracted with dichloromethane (5 mL×3), dried over anhydrous sodium sulfate, filtered and concentrated, the crude product was purified by preparative thin layer chromatography (PE/EtOAc=2:1) to give the compound 4g.

MS-ESI calculated value [M−56+H]⁺ 319, measured value 319.

¹H NMR (400 MHz, CDCl₃) δ 7.37-7.36 (m, 5H), 5.18-5.09 (m, 2H), 3.68-3.59 (m, 2H), 3.48-3.39 (m, 2H), 3.67-3.35 (m, 1H), 2.84-2.80 (m, 1H), 1.99-1.95 (m, 2H), 1.47-1.29 (m, 15H).

The Sixth Step

The compound 4g (62 mg, 0.17 mmol) and 1 mL dichloromethane were added into a 25 mL round bottom flask, then under the protection of nitrogen, trifluoroacetate (190 mg, 1.67 mmol) was added dropwise, then stirred at 25° C. for 1 hr. After completion of the reaction, the reaction mixture was concentrated directly to give the compound 4h (46 mg, a crude product).

MS-ESI calculated value [M+H]⁺ 275, measured value 275.

The Seventh Step

The compound 4h (46 mg, 0.17 mmol), N, N-diisopropylethylamine (65 mg, 0.5 mmol) and 1.5 mL dichloromethane were added into a 25 mL round bottom flask, and under the protection of nitrogen, isoquinoline sulfonyl chloride 1i (49 mg, 0.22 mmol) was added dropwise slowly at 0° C., then stirred at 25° C. for 2 hrs. After completion of the reaction, the reaction mixture was concentrated directly, the crude product was purified by preparative thin layer chromatography (PE/EtOAc=1:1) to give the compound 4i.

MS-ESI calculated value [M+H]⁺ 466, measured value 466.

¹H NMR (400 MHz, CDCl₃) δ 9.34-9.33 (m, 1H), 8.68-8.66 (m, 1H), 8.49-8.39 (m, 2H), 8.21-8.19 (m, 1H), 7.71-7.66 (m, 1H), 7.34-7.28 (m, 5H), 5.09-5.05 (m, 2H), 3.64-3.49 (m, 2H), 3.33-3.28 (m, 1H), 3.08-2.97 (m, 3H), 2.81-2.80 (m, 1H), 2.54-2.52 (m, 1H), 1.32-1.27 (m, 6H).

The Eighth Step

The compound 4i (32 mg, 0.07 mmol) and 1 mL trifluoroacetate were added into a 5 mL microwave tube, sealed, then stirred at 100° C. in a microwave reactor for 1 hr. After completion of the reaction, the reaction mixture was concentrated directly, the crude product was purified by preparative liquid chromatography HPLC to give the compound 4.

MS-ESI calculated value [M+H]⁺ 332, measured value 332.

¹H NMR (400 MHz, CDCl₃) δ 9.42 (s, 1H), 8.69-8.68 (m, 1H), 8.60-8.59 (m, 1H), 8.56-8.54 (m, 1H), 8.45 (d, J=8.0 Hz, 1H), 7.86 (t, J=8.0 Hz, 1H), 3.82-3.77 (m, 1H), 3.26-3.20 (m, 2H), 2.98 (m, 1H), 2.97 (m, 1H), 2.54-2.44 (m, 3H), 1.41 (s, 6H).

Embodiment 5

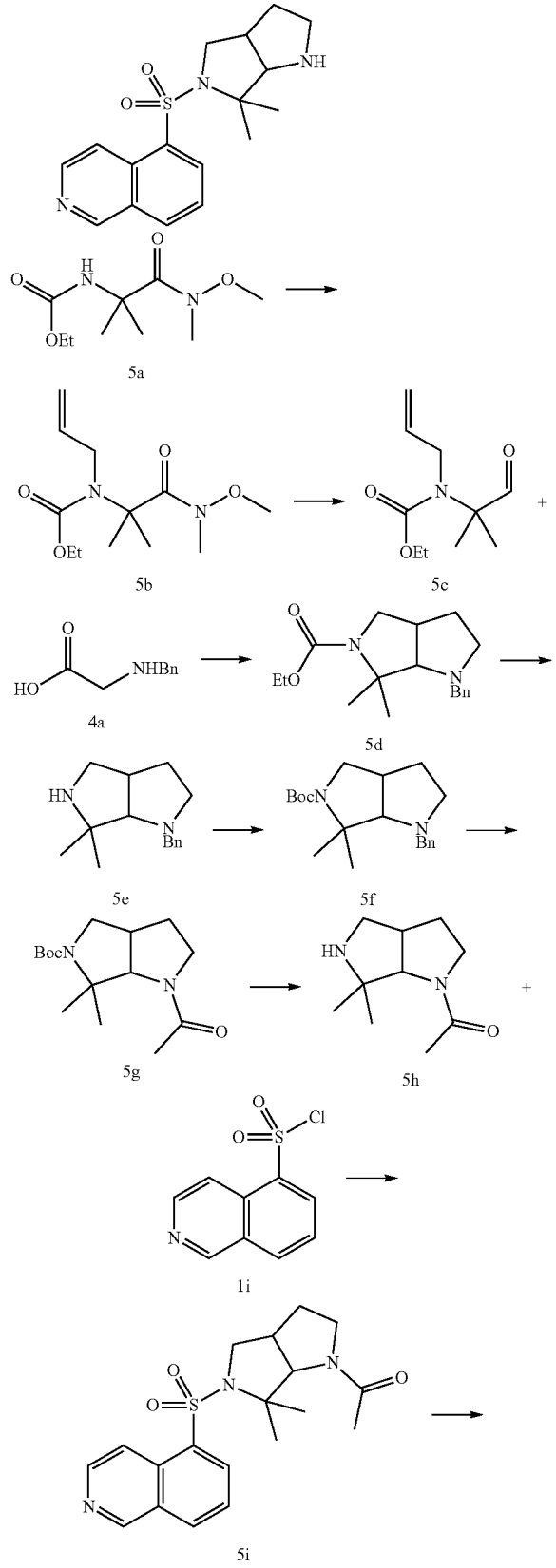

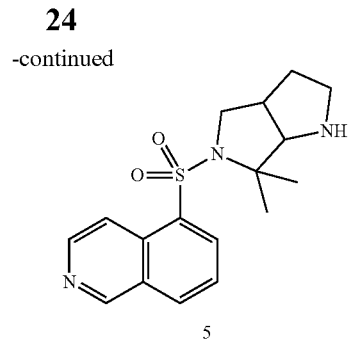

The First Step 5a (4.00 g, 18.33 mmol) was dissolved in 20 mL N,N-dimethylformamide, sodium hydrogen (0.88 g, 21.99 mmol, 60%) was added dropwise slowly under the protection of nitrogen, the temperature was maintained at 0° C. The mixture was stirred at 25° C. for 10 mins, bromopropene (4.43 g, 36.66 mmol) was added into the reaction mixture. The mixture was continued to be stirred at 25° C. for 3 hrs. After completion of the reaction, the reaction mixture was quenched by saturated ammonium chloride solution 20 mL at 0° C., water (40 mL), EtOAc (40 mL×3) were added, and the organic phases were combined and washed with saturated brine (50 mL×1), dried over anhydrous sodium sulfate, filtered and concentrated, the crude product was purified by column chromatography (PE/EtOAc=100-0%) to give 5b.

The Second Step 5b (2.50 g, 9.68 mmol) was dissolved in THF (40 mL), under the protection of nitrogen, diisobutylaluminum hydride (1 M, 17.4 mL) was added dropwise at −78° C. The reaction mixture obtained was stirred at −78° C. for 6 hrs. After completion of the reaction, the reaction mixture was quenched by saturated ammonium chloride solution (20 mL) and HCl (1 N, 10 mL) at 25° C., water (20 mL) and EtOAc (40 mL×3) were added, the organic phases were combined and washed with saturated brine (40 mL×1), dried over anhydrous sodium sulfate, filtered and concentrated, the crude product was purified by column chromatography (PE/EtOAc=100-0%) to give 5c.
$^1$H NMR (400 MHz, CDCl$_3$) δ 9.32 (s, 1H), 5.90-5.78 (m, 1H), 5.23-5.11 (m, 2H), 4.14 (q, J=8.0 Hz, 2H), 3.95 (d, J=4.0 Hz, 2H), 1.27 (s, 6H), 1.23 (t, J=8.0 Hz, 3H).

The Third Step 5c (1.50 g, 7.53 mmol) and glycine 4a (2.49 g, 15.06 mmol) were dissolved in 20 mL toluene. The reaction mixture obtained was stirred at 130° C. for 16 hrs. After completion of the reaction, water (10 mL) was added into the reaction mixture, then the mixture was extracted with EtOAc (15 mL×3), the organic phases were combined and washed with saturated brine (20 mL×1), dried over anhydrous sodium sulfate, filtered and concentrated, the crude product was purified by column chromatography (PE/EtOAc=100-0%) to give 5d.
$^1$H NMR (400 MHz, CDCl$_3$) δ 7.38-7.34 (m, 2H), 7.30 (t, J=8.0 Hz, 2H), 7.26-7.20 (m, 1H), 4.16 (d, J=8.0 Hz, 2H), 3.97 (d, J=4.0 Hz, 2H), 3.64-3.55 (m, 1H), 3.48-3.40 (m, 1H), 3.29 (d, J=4.0 Hz, 1H), 3.11-2.98 (m, 2H), 2.84-2.73 (m, 1H), 2.45-2.36 (m, 1H), 1.87-1.93 (m, 1H), 1.30 (s, 6H), 1.25 (s, 3H).

The Fourth Step 5d (400 mg, 1.32 mmol) was dissolved in 20 mL acetonitrile, then trimethyl iodosilane (2.65 g, 13.23 mmol) was added dropwise. The reaction mixture obtained was stirred at 25° C. for 6 hrs. After completion of the reaction, the reaction mixture was quenched by adding 20 mL water, EtOAc (20 mL×3), the organic phases were combined and washed with saturated brine (30 mL×1), dried over anhydrous sodium sulfate, filtered and concentrated to give a crude product of 5e, which was used directly in the next step.

The Fifth Step 5e (250 mg, 1.09 mmol) was dissolved in 10 mL dichloromethane, then di-tert-butyl dicarbonate (474 mg, 2.17 mmol) and diisopropylethylamine (281 mg, 2.17 mmol) were added dropwise sequentially. The mixture obtained was stirred at 25° C. for 16 hrs. After completion of the reaction, water (10 mL) was added to quench the reaction, dichloromethane (20 mL×2), the organic phases were combined and washed with saturated brine (20 mL×1), dried over anhydrous sodium sulfate, filtered and concentrated, the crude product obtained was purified by preparative thin layer chromatography (EtOAc/PE=5/1) to give 5f.

The Sixth Step 5f (300 mg, 0.91 mmol) and acetic anhydride (185 mg, 1.82 mmol) were dissolved in EtOAc (30 mL), under the protection of nitrogen protection, palladium on carbon (60 mg, 10%) was added. The reaction mixture obtained was replaced with hydrogen and stirred under hydrogen atmosphere (50 PSI) at 50° C. for 3 hrs. After completion of the reaction, the reaction mixture was filtered and concentrated to give a crude product of 5g.

MS-ESI calculated value [M+H]⁺ 283, measured value 283.

The Seventh Step

Ethyl acetate-hydrochloride (20 mL, 4 M) was added dropwise into a solution of 5g (250 mg, 0.89 mmol) in 5 mL EtOAc at 25° C. The reaction mixture obtained was continued to be stirred for 0.5 hrs. After completion of the reaction, the solvent was removed directly to give a crude product of 5h, which was used directly in the next step.

The Eighth Step

The compound 1i (150 mg, 0.66 mmol) and 5h (200 mg, hydrochloride) were dissolved in 5 mL dichloromethane, then diisopropylethylamine (142 mg, 1.10 mmol) was added dropwise. The reaction mixture obtained was stirred for 16 hrs at 25° C. After completion of the reaction, the solvent was removed by concentration, water (5 mL) was added, then extracted by EtOAc (10 mL×2), the organic phases were combined and washed by saturated brine (15 mL×1), dried over anhydrous sodium sulfate, filtered and concentrated, the crude product obtained was purified by preparative thin layer chromatography (EtOAc) to give 5i.

MS-ESI calculated value [M+H]⁺ 374, measured value 374.

The Ninth Step 5i (100 mg, 0.66 mmol) was dissolved in the mixture of ethanol (0.5 mL) and water (1 mL), sodium hydrochloride (321 mg, 8.03 mmol) was added. The reaction mixture obtained was stirred at 100° C. for 16 hrs. After completion of the reaction, the pH of the mixture was adjusted to neutral by diluted hydrochloric acid (1 N), then purified by high performance liquid chromatography to give the compound 5.

MS-ESI calculated value [M+H]⁺ 332, measured value 332.

¹H NMR (400 MHz, CD₃OD) δ 9.38 (s, 1H), 8.66-8.54 (m, 3H), 8.43-8.37 (m, 1H), 7.82 (t, J=8.0 Hz, 1H), 3.75-3.80 (m, 1H), 3.29-3.20 (m, 2H), 3.13-3.07 (m, 1H), 2.89-2.68 (m, 3H), 1.97-1.88 (m, 1H), 1.49 (s, 3H), 1.36 (s, 3H).

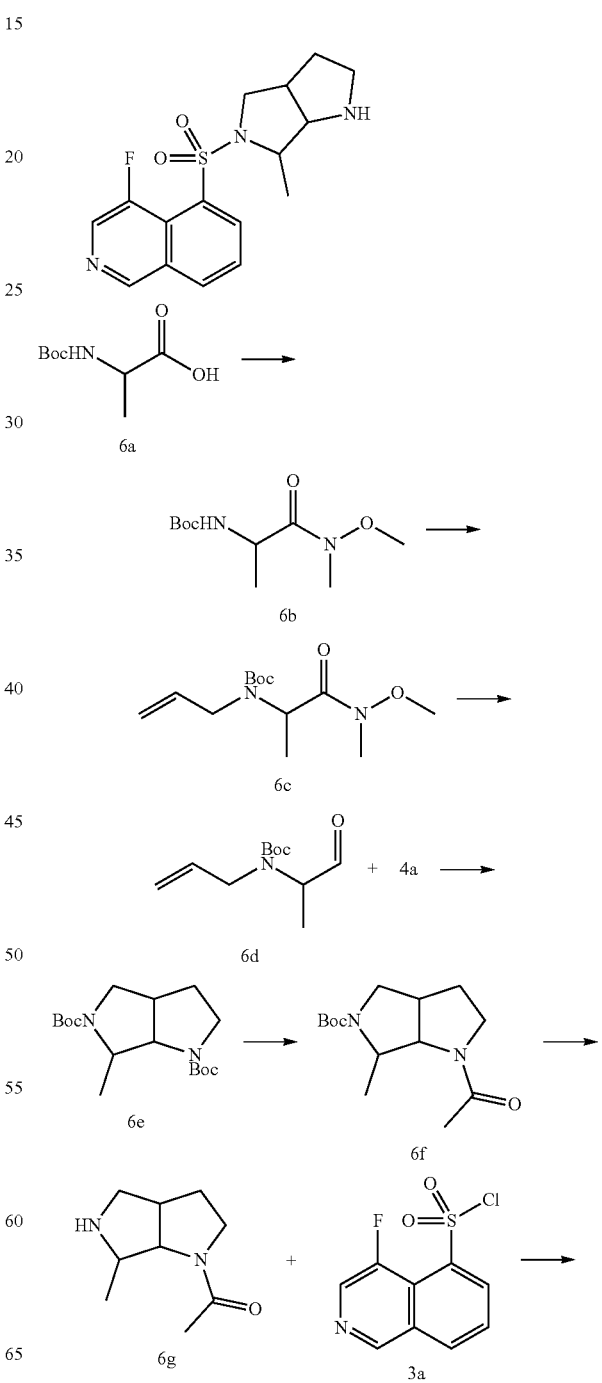

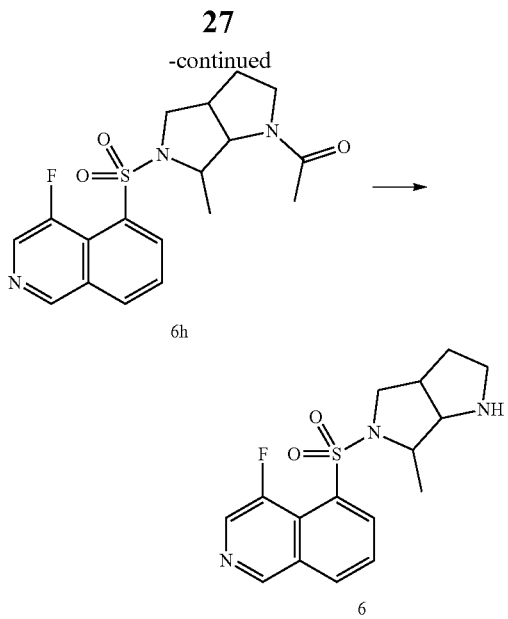

6h

6

Embodiment 6

The First Step

At 0° C., N-methoxymethylamine hydrochloride (8.83 g, 90.57 mmol) was added into a solution of the compound 6a (15.58 g, 82.34 mmol), HATU (32.87 g, 86.46 mmol) and diisopropylethylamine (22.35 g, 172.91 mmol) in 200 mL dichloromethane. The reaction mixture obtained was stirred at 25° C. for 16 hrs. After completion of the reaction, 200 mL water was added into the reaction mixture, and the pH of the mixture was adjusted to 14 with 1 N aqueous sodium hydrochloride solution, then extracted with dichloromethane (200 mL×2), the organic phase was dried over anhydrous sodium sulfate, filtered and concentrated, the crude product was purified by silica gel column (PE/EtOAc=100-0%) to give the compound 6b.

$^1$H NMR (400 MHz, CDCl$_3$) δ 5.25 (s, 1H), 4.69 (s, 1H), 3.78 (s, 3H), 3.22 (s, 3H), 1.45 (s, 9H), 1.32 (d, J=8.0 Hz, 3H).

The Second Step

At 0° C. and under the protection of nitrogen, sodium hydrogen (4.30 g, 107.51 mmol, 60%) was added in batch into a solution of the compound 6b (14.69 g, 63.24 mmol) in 200 mL N, N-dimethylformamide, when the addition was finished, the mixture was continued stirring for another 10 mins, then 3-bromopropene (19.13 g, 158.10 mmol) was added dropwise at 0° C. The reaction mixture obtained was reacted at 15° C. for 22 hrs. After completion of the reaction, 200 mL saturated ammonium chloride aqueous solution was added into the mixture, 200 mL water was added, the mixture was extracted by EtOAc (200 mL×2). The organic phase was washed with saturated brine (300 mL×3), dried over anhydrous sodium sulfate, filtered and concentrated, the crude product obtained was purified by silica gel column (PE/EtOAc=100-0%) to give the compound 6c.

$^1$H NMR (400 MHz, CDCl$_3$) δ 5.86-5.81 (m, 1H), 5.30-5.25 (m, 1H), 5.14-5.04 (m, 2H), 3.95-3.83 (m, 2H), 3.74 (s, 3H), 3.16 (s, 3H), 1.44 (s, 9H) 1.31 (d, J=8.0 Hz, 3H).

The Third Step

At −78° C. and under the protection of nitrogen, DIBAL-H (97.90 mmol, 97.9 mL, 1 M) was added into a solution of the compound 6c (13.33 g, 48.95 mmol) in 200 mL THF. The reaction mixture obtained was stirred at 20° C. for 2 hrs. After completion of the reaction, 400 mL saturated potassium tartrate, 200 mL water and 300 mL EtOAc were added into the reaction mixture, then extracted with EtOAc (300 mL×2). The organic phase was washed with saturated brine, dried over anhydrous sodium sulfate, filtered and concentrated to give directly a crude product of the compound 6d.

$^1$H NMR (400 MHz, CDCl$_3$) δ 9.56 (s, 1H), 5.87-5.81 (m, 1H), 5.30-5.10 (m, 3H), 3.85-3.76 (m, 1H), 3.56-3.49 (m, 1H), 1.46 (s, 9H) 1.34 (d, J=8.0 Hz, 3H).

The Fourth Step

A solution of the compound 6d (12.96 g, 60.77 mmol) and the compound 4a (25.10 g, 151.93 mmol) in 307 mL toluene was heated to 135° C. then reacted for 24 hrs. After completion of the reaction, 300 mL water was added into the reaction system, then extracted with EtOAc (300 mL×4), the organic phase was washed with saturated brine (300 mL×3), dried over anhydrous sodium sulfate, filtered and concentrated, the crude product obtained was purified by silica gel column (PE/EtOAc=100-0%) to give the compound 6e.

$^1$H NMR (400 MHz, CDCl$_3$) δ 7.26-7.16 (m, 5H), 3.96-3.61 (m, 2H), 3.45-3.20 (m, 3H), 2.98-2.84 (m, 1H), 2.73-2.59 (m, 2H), 2.20-2.13 (m, 1H) 1.97-1.84 (m, 1H), 1.58-1.46 (m, 1H), 1.38 (s, 9H), 1.01-0.85 (m, 3H).

The Fifth Step

Under the protection of nitrogen, dry palladium on carbon (1.00 g, 10%) was added into a solution of the compound 6e (7.00 g, 22.12 mmol) and Ac$_2$O (4.52 g, 4.1 mL, 44.24 mmol) in 100 mL EtOAc. The reaction mixture was replaced with hydrogen for 3 times. The reaction mixture obtained was stirred to react under hydrogen atmosphere (50 PSI) at 50° C. for 10 hrs. After completion of the reaction, the reaction mixture was filtered and concentrated, the crude product was purified by column chromatography (PE/EtOAc=100-0%) to give the compound 6f. MS-ESI calculated value [M+H−100]$^+$ 269, measured value 269.

$^1$H NMR (400 MHz, CDCl$_3$) δ 4.03-4.01 (m, 2H), 3.59-3.50 (m, 2H), 3.48-3.35 (m, 2H), 2.94-2.93 (m, 1H), 2.09-2.02 (m, 4H), 1.80-1.70 (m, 1H), 1.45 (s, 9H), 1.28-1.12 (m, 3H).

The Sixth Step

At 0° C. and under the protection of nitrogen, trifluoroacetate (36.87 g, 323.40 mmol) was added dropwise into a solution of the compound 6f (4.34 g, 16.17 mmol) in 20 mL dichloromethane. The reaction mixture obtained was stirred at 25° C. for 12 hrs. After completion of the reaction, the mixture was directly concentrated, 20 mL saturated aqueous sodium carbonate solution was added slowly into the crude product obtained at 0° C., extracted with EtOAc (50 mL×3), then washed with saturated brine (20 mL×3), the organic phase was dried over anhydrous sodium sulfate, filtered and concentrated to give a crude product of the compound 6g.

MS-ESI calculated value [M+H]$^+$ 169, measured value 169.

$^1$H NMR (400 MHz, CD$_3$OD) δ 4.00-3.91 (m, 2H), 3.69-3.52 (m, 2H), 3.41-3.04 (m, 3H), 2.71-2.61 (m, 3H), 2.09-2.02 (m, 4H), 1.83-1.76 (m, 1H).

The Seventh Step

The compound 6h was obtained from 6g (2.08 g, 12.37 mmol) and the compound 3a (3.04 g, 12.37 mmol) using the synthesis method in the seventh step of the embodiment 1.

MS-ESI calculated value [M+H]$^+$ 378, measured value 378.

$^1$H NMR (400 MHz, CDCl$_3$) δ 9.17 (s, 1H), 8.62-8.55 (m, 2H), 8.23 (d, J=8.0 Hz, 1H), 7.73 (t, J=8.0 Hz, 1H), 4.33-4.22 (m, 1H), 4.12-4.02 (m, 1H) 3.81-3.71 (m, 1H), 3.70-3.60 (m, 1H), 3.58-3.42 (m, 1H), 3.07-2.96 (m, 1H), 2.05 (s, 3H), 1.95-1.83 (m, 1H), 1.55-1.45 (m, 1H), 1.44-1.35 (m, 1H), 1.07 (d, J=8.0 Hz, 3H).

The Eighth Step

Concentrated hydrochloric acid 25 mL (12 M) was added into a solution of the compound 6h (2.26 g, 5.99 mmol) in the mixed solvent of 12.5 mL ethanol and 25 mL water. The reaction mixture obtained was reacted at 100° C. for 24 hrs. After completion of the reaction, the reaction mixture was concentrated to remove ethanol, then the pH of the mixture was adjusted to 7 with saturated sodium bicarbonate aqueous solution, and a solid precipitated, filtered to give a crude product, then purified by high performance liquid chromatography to give the compound 6.

MS-ESI calculated value [M+H]+ 336, measured value 336.

$^1$H NMR (400 MHz, CDCl$_3$) δ 9.15 (s, 1H), 8.82 (d, J=8.0 Hz, 1H), 8.58 (d, J=8.0 Hz, 1H), 8.22 (d, J=8.0 Hz, 1H), 7.72 (t, J=8.0 Hz, 1H), 4.04-3.92 (m, 1H), 3.81-3.76 (m, 1H), 3.47 (d, J=8.0 Hz, 1H), 3.34-3.30 (m, 1H), 3.15-3.05 (m, 1H), 2.95-2.85 (m, 2H), 2.03-1.96 (m, 1H), 1.60-1.54 (m, 1H), 1.20 (d, J=8.0 Hz, 3H).

6-1 and 6-2

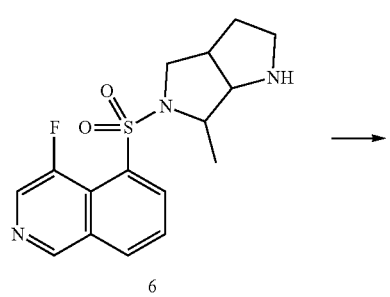

6

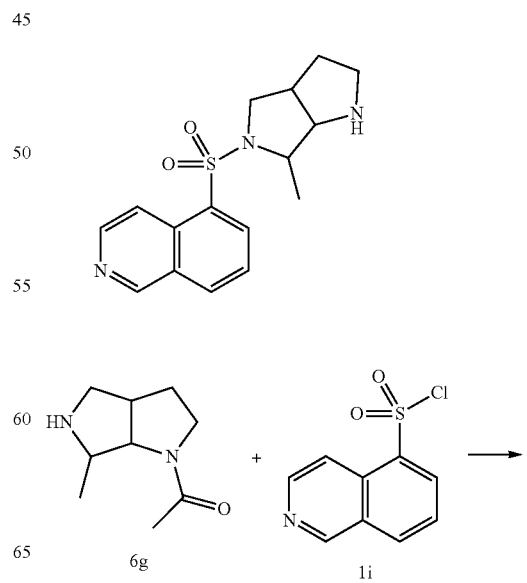

6-1 and 6-2

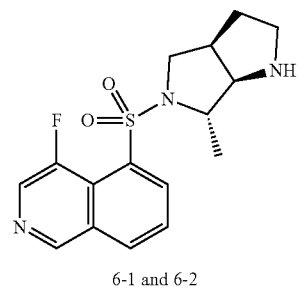

6-1 and 6-2

SFC Analysis Conditions:

column: Chiralpak AD-3 100×4.6 mm I.D., 3 μm mobile phase: A: CO$_2$ B: methanol (0.05% DEA)

gradient: B went from 5% to 40% in 4.5 mins, then was maintained at 40% for 2.5 mins, then B was maintained at 5% for 1 min, flow rate: 2.8 mL/min column temperature: 40° C.

6-1 retention time t=3.818 mins $^1$H NMR (400 MHz, CDCl$_3$) δ 9.13 (s, 1H), 8.81-8.80 (m, 1H), 8.56 (brs, 1H), 8.21-8.19 (m, 1H), 7.70 (brs, 1H), 4.01-4.00 (m, 1H), 3.77-3.75 (m, 1H), 3.46-3.45 (m, 1H), 3.31 (brs, 1H), 3.06 (brs, 1H), 2.86 (brs, 2H), 2.07 (brs, 1H), 1.57 (brs, 1H), 1.20-1.19 (m, 3H). MS-ESI calculated value [M+H]$^+$ 336, measured value 336.

6-2 retention time t=4.111 mins $^1$H NMR (400 MHz, CDCl$_3$) δ 9.13 (s, 1H), 8.81-8.80 (m, 1H), 8.55 (brs, 1H), 8.20-8.19 (m, 1H), 7.70 (brs, 1H), 4.01 (brs, 1H), 3.77 (brs, 1H), 3.46 (brs, 1H), 3.31 (brs, 1H), 3.06 (brs, 1H), 2.87 (brs, 2H), 2.07 (brs, 1H), 1.56 (brs, 1H), 1.19 (brs, 3H).

MS-ESI calculated value [M+H]$^+$ 336, measured value 336.

Embodiment 7

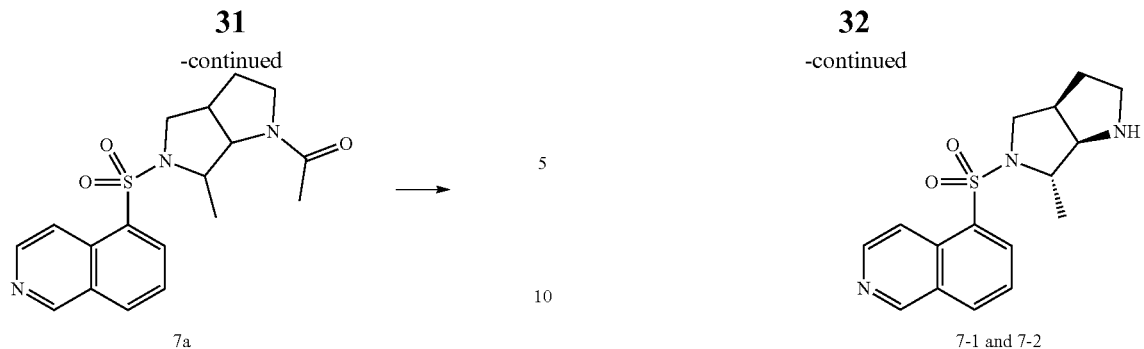

The First Step

The compound 7 was obtained from the compound 6g (1.00 g, 5.94 mmol) and the compound 1i (1.73 g, 6.53 mmol) by two-step of reaction using the synthesis in embodiment 6. MS-ESI calculated value [M+H]$^+$ 360, measured value 360.

$^1$H NMR (400 MHz, CDCl$_3$) δ 9.35 (s, 1H), 8.71-8.69 (m, 1H), 8.56-8.50 (m, 2H), 8.20 (d, J=8.4 Hz, 1H), 7.70 (d, J=8.0 Hz, 1H), 3.88-3.87 (m, 1H), 3.68-3.64 (m, 1H), 3.42-3.40 (m, 1H), 3.18-3.17 (m, 1H), 2.82-2.73 (m, 3H), 1.90-1.86 (m, 1H), 1.43-1.41 (m, 1H), 1.22-1.21 (m, 3H).

7-1 and 7-2

SFC Analysis Conditions:
column: Chiralpak AD-3 100×4.6 mm I.D., 3 um;
mobile phase: A: CO$_2$ B: methanol (0.05% DEA);
gradient: B went from 5% to 40% in 5 mins, then was maintained at 40% for 2.5 mins, then B was maintained at 5% for 1 min;
flow rate: 2.5 mL/min;
column temperature: 35° C.

7-1 retention time t=4.062 mins $^1$H NMR (400 MHz, CDCl$_3$) δ 9.27 (s, 1H), 8.63-8.61 (m, 1H), 8.49-8.42 (m, 2H), 8.13 (d, J=8.0 Hz, 1H), 7.62 (t, J=8.0 Hz, 1H), 3.78-3.77 (m, 1H), 3.61-3.56 (m, 1H), 3.32-3.31 (m, 1H), 3.10-3.06 (m, 1H), 2.67-2.64 (m, 3H), 1.81-1.76 (m, 1H), 1.33-1.32 (m, 1H), 1.15-1.14 (m, 3H).

MS-ESI calculated value [M+H]$^+$ 318, measured value 318.

7-2 retention time t=4.303 mins $^1$H NMR (400 MHz, CDCl$_3$) δ 9.27 (s, 1H), 8.63-8.61 (m, 1H), 8.49-8.42 (m, 2H), 8.12 (d, J=8.4 Hz, 1H), 7.62 (t, J=8.0 Hz, 1H), 3.78-3.76 (m, 1H), 3.61-3.56 (m, 1H), 3.32-3.30 (m, 1H), 3.09-3.05 (m, 1H), 2.67-2.64 (m, 3H), 1.81-1.75 (m, 1H), 1.33-1.32 (m, 1H), 1.15-1.14 (m, 3H).

MS-ESI calculated value [M+H]$^+$ 318, measured value 318.

Embodiment 8

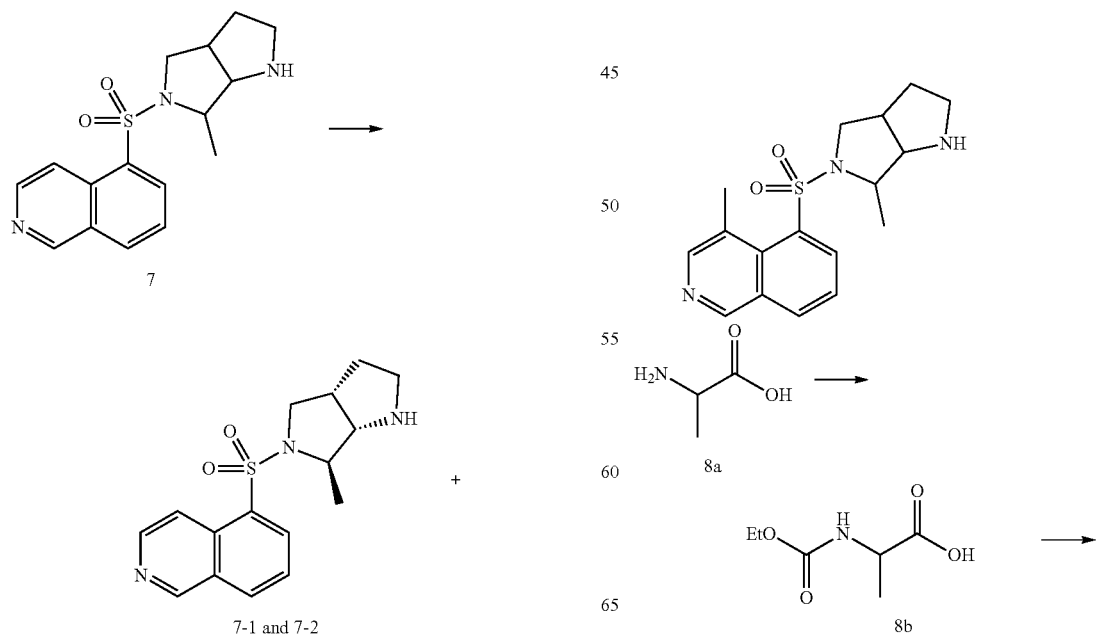

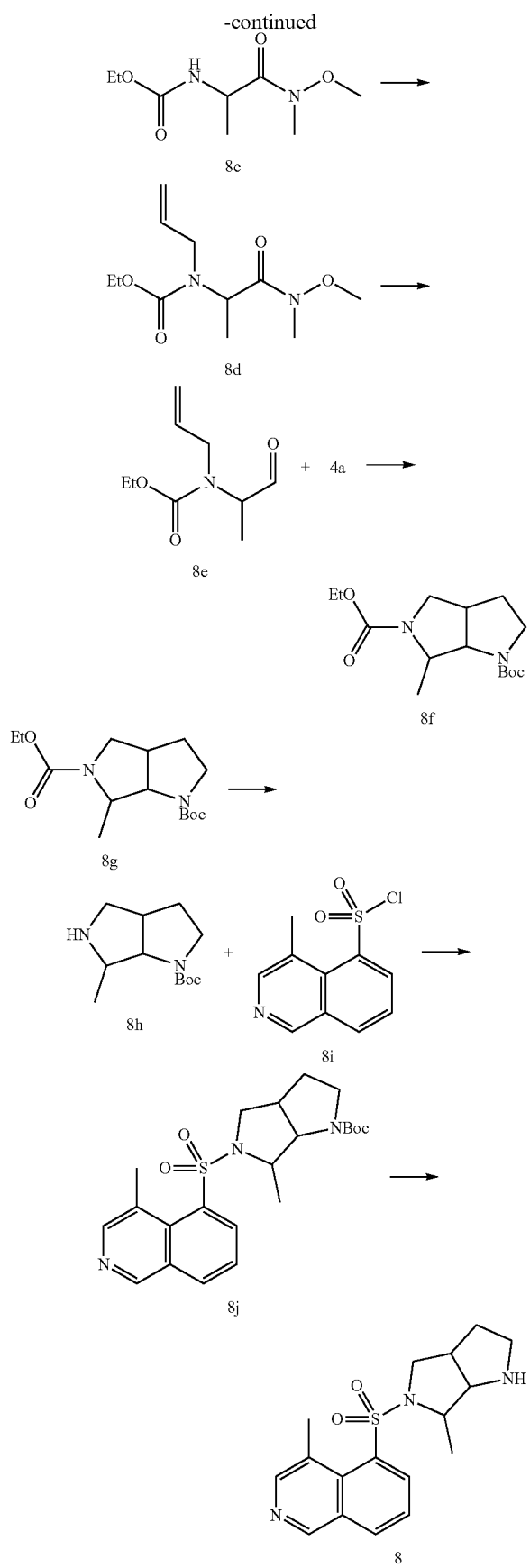

The First Step

At 25° C., ethyl chloroformate (84.9 g, 782.34 mmol) was added dropwise into a solution of 8a (50.00 g, 561.23 mmol) and sodium bicarbonate (141.45 g, 1.68 mol) in the mixed solvent of 250 mL THF and 250 mL water. The reaction mixture obtained was stirred to react at 25° C. for 48 hrs. After completion of the reaction, the mixture was filtered and concentrated to remove THF, after the concentration, water (50 mL) was added, then extracted with methyl ter-butyl ether (200 mL×1). The pH of the aqueous phase was adjusted to 1 then extracted with EtOAc (200 mL×2), the organic phases were combined, dried over anhydrous sodium sulfate, filtered and concentrated to give a crude product of the compound 8b.

$^1$H NMR (400 MHz, CDCl$_3$) δ 5.19 (s, 1H), 4.43-4.38 (m, 1H), 4.16-4.12 (m, 2H), 1.47 (d, J=7.6 Hz, 3H), 1.27 (t, J=7.2 Hz, 3H).

The Second Step

At 0° C. and under the protection of nitrogen, propanephosphonic anhydride solution (473.83 g, 744.6 mmol, 50%) and diisopropylethylamine (128.31 g, 992.80 mmol) were added sequentially into a solution of the compound 8b (40.00 g, 248.20 mmol) in 500 mL EtOAc. The reaction mixture obtained was stirred at 25° C. for 10 mins, then N-methoxymethylamine hydrochloride (26.63 g, 273.02 mmol) was added. The reaction mixture was stirred to react at 25° C. for 16 hrs. After completion of the reaction, water (300 mL) was added into the reaction mixture, then the mixture was extracted with EtOAc (200 mL×2), the organic phases were combined, dried over anhydrous sodium sulfate, filtered and concentrated, the crude product was purified by column chromatography (PE/EtOAc=100-0%) to give the compound 8c.

$^1$H NMR (400 MHz, CDCl$_3$) δ 5.43-5.42 (m, 1H), 4.73-4.69 (m, 1H), 4.08 (t, J=6.8 Hz, 2H), 3.76 (s, 3H), 3.20 (s, 3H), 1.32 (d, J=6.8 Hz, 3H), 1.22 (d, J=7.2 Hz, 3H).

The Third Step

At 0° C. and under the protection of nitrogen, sodium hydrogen (8.46 g, 211.54 mmol, 60%) was added in batch into a solution of 3-bromopropene (31.99 g, 264.42 mmol) in N, N-dimethylformamide (400 mL). The reaction mixture was stirred for 10 mins then the compound 8c (36.00 g, 176.28 mmol) was added. The reaction mixture obtained was continued stirring and reacting at 20° C. for 5 hrs. After the completion of the reaction, saturated ammonium chloride solution (300 mL) and water (200 mL) were added into the mixture, then extracted with EtOAc (400 mL×3), the organic phases were combined and washed with saturated brine (400 mL×3), dried over anhydrous sodium sulfate, filtered and concentrated, the crude product was purified by column chromatography (PE/EtOAc=100-0%) to give the compound 8d.

$^1$H NMR (400 MHz, CDCl$_3$) δ 5.83-5.77 (m, 1H), 5.26-5.01 (m, 3H), 4.11-4.07 (m, 2H), 3.97-3.90 (m, 2H), 3.73-3.66 (m, 3H), 3.17-2.95 (m, 3H), 1.36-1.29 (m, 3H), 1.24-1.19 (m, 3H).

The Fourth Step

At −78° C. and under the protection of nitrogen, diisobutylaluminum hydride (81.9 mL, 1 M) was added dropwise into a solution of the compound 8d (10.00 g, 40.93 mmol) in 150 mL THF. After completion of the addition, the mixture was stirred to react at 20° C. for 3 hrs. After completion of the reaction, saturated potassium sodium tartrate solution (500 mL) and water (200 mL) were added slowly into the reaction mixture, then extracted with EtOAc (300 mL×3), the organic phases were combined and washed by saturated brine, dried over anhydrous sodium sulfate, filtered and concentrated, the crude product was purified by column chromatography (PE/EtOAc=100-0%) to give the compound 8e.

$^1$H NMR (400 MHz, CDCl$_3$) δ 9.51 (s, 1H), 5.81-5.74 (m, 1H), 5.18-5.09 (m, 2H), 4.12-4.04 (m, 3H), 3.95-3.74 (m, 2H), 1.34-1.28 (m, 3H), 1.22-1.13 (m, 3H).

The Fifth Step

The compound 8f was obtained from the compound 8e (4.65 g, 25.11 mmol) and the compound 4a (8.29 g, 50.21 mmol) using the synthesis method in the third step of the embodiment 5.

MS-ESI calculated value [M+H]$^+$ 289, measured value 289.

$^1$H NMR (400 MHz, CDCl$_3$) δ 7.21-7.13 (m, 5H), 4.06-4.01 (m, 2H), 3.81 (brs, 2H), 3.49-3.46 (m, 1H), 3.44-3.38 (m, 2H), 2.88 (s, 1H), 2.69 (brs, 2H), 2.17-2.11 (m, 1H), 1.95-1.85 (m, 1H), 1.55-1.43 (m, 1H), 1.19-1.15 (m, 3H), 1.02-0.95 (m, 3H).

The Sixth Step

Under the protection of nitrogen, wet palladium on carbon (200 mg, 10%) was added into a solution of the compound 8f (2.00 g, 6.94 mmol) and di-tert-butyl dicarbonate (3.03 g, 13.88 mmol) in 150 mL methanol. The reaction mixture obtained was replaced with hydrogen then under hydrogen atmosphere (50 PSI) and stirred to react at 50° C. for 24 hrs. After completion of the reaction, filtered and concentrated, the crude product was purified by silica get column (PE/EtOAc=100-0%) to give the compound 8g.

$^1$H NMR (400 MHz, CDCl$_3$) δ 4.15-4.09 (m, 3H), 3.86-5.75 (m, 1H), 3.60-3.55 (m, 2H), 3.36-3.34 (m, 2H), 3.02-2.91 (m, 1H), 1.98-1.93 (m, 1H), 1.73 (s, 1H), 1.48 (s, 9H), 1.28-1.23 (m, 3H).

The Seventh Step

The compound 8g (250 mg, 0.84 mmol) was dissolved in the mixed solvent of ethanol (4 mL) and water (3 mL), potassium hydroxide (1.50 g, 26.81 mmol) was then added. The reaction mixture obtained was stirred at 120° C. for 40 hrs. After completion of the reaction, the reaction mixture was concentrated to remove ethanol, then water (5 mL) was added, extracted with dichloromethane (5 mL×2), the organic phases were combined and washed with saturated brine, dried over anhydrous sodium sulfate, filtered and concentrated, the crude product was purified by column chromatography (dichloromethane/methanol=100-0%) to give the compound 8h.

$^1$H NMR (400 MHz, CDCl$_3$) δ 3.86-3.57 (m, 2H), 3.28-3.23 (m, 1H), 3.07-3.10 (m, 2H), 2.77 (s, 1H), 2.60-2.55 (m, 1H), 1.83-2.75 (m, 2H), 1.65-1.53 (m, 1H), 1.41 (s, 9H), 1.20-1.13 (m, 3H).

The Eighth Step

The compound 8j was obtained from the compound 8h (81 mg, 0.36 mmol) and the compound 8i (200 mg, 0.72 mmol) using the synthesis method in the seventh step of embodiment 1.

MS-ESI calculated value [M+H]$^+$ 432, measured value 432.

The Ninth Step

At 20° C., trifluoroacetate (2 mL) was added dropwise into a solution of the compound 8j (109 mg, 0.25 mmol) in 6 mL dichloromethane, the reaction mixture was continued stirring for 2 hrs. After completion of the reaction, the reaction mixture was directly concentrated, the crude product was purified by high performance liquid chromatography to give the compound 8.

MS-ESI calculated value [M+H]$^+$ 332, measured value 332.

1H NMR (400 MHz, CD3OD) δ 9.20 (s, 1H), 8.80 (d, J=7.2 Hz, 1H), 8.48 (s, 1H), 8.37 (d, J=8.4 Hz, 1H), 7.77 (t, J=8.0 Hz, 1H), 4.12-4.10 (m, 1H), 3.82-3.78 (m, 1H), 3.62-3.60 (m, 1H), 3.41-3.37 (m, 1H), 3.62-3.60 (m, 1H), 3.18 (brs, 1H), 3.08-3.05 (m, 5H), 2.09-2.04 (m, 1H), 1.80-1.79 (m, 1H), 1.34-1.32 (m, 3H).

Embodiment 9

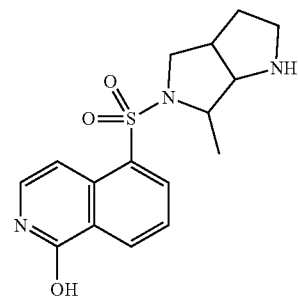

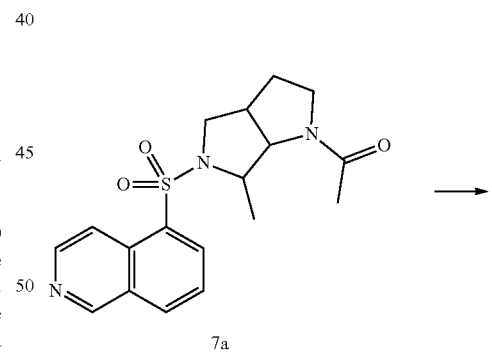

7a

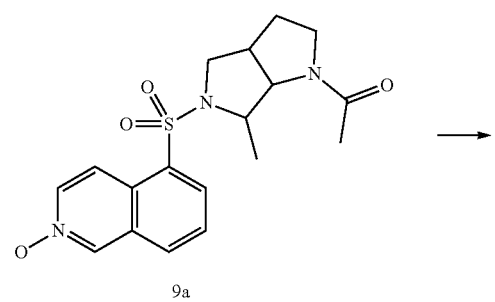

9a

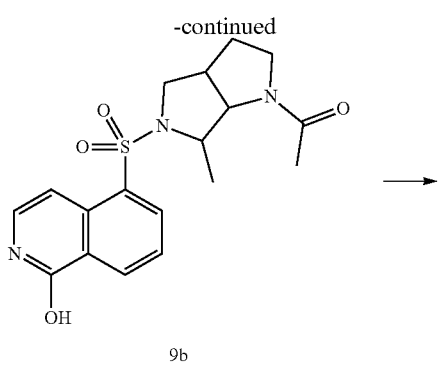

9b

<sup>1</sup>H NMR (400 MHz, CDCl$_3$) δ 8.68 (d, J=7.2 Hz, 1H), 8.37 (d, J=7.6 Hz, 1H), 7.61-7.57 (m, 1H), 7.53-7.48 (m, 1H), 7.25-7.23 (m, 1H), 4.32-4.31 (m, 1H), 3.97-3.95 (m, 1H), 3.71-3.67 (m, 1H), 3.36-3.28 (m, 1H), 3.20-3.16 (m, 1H), 3.02-2.98 (m, 2H), 1.93-1.92 (m, 1H), 1.84 (s, 3H), 1.74-1.70 (m, 1H), 1.26 (d, J=6.8 Hz, 3H).

The Third Step

The compound 9 was obtained from the compound 9b (53 mg, 0.14 mmol) using the synthesis method in the eighth step of embodiment 6.

MS-ESI calculated value [M+H]$^+$ 334, measured value 334.

<sup>1</sup>H NMR (400 MHz, CD$_3$OD) δ 8.61 (d, J=8.0 Hz, 1H), 8.41 (d, J=6.4 Hz, 1H), 7.66 (t, J=8.0 Hz, 1H), 7.45 (d, J=7.6 Hz, 1H), 7.35 (d, J=7.2 Hz, 1H), 3.81-3.79 (m, 1H), 3.64-3.59 (m, 1H), 3.50-3.39 (m, 1H), 3.11-3.07 (m, 1H), 2.88-2.86 (m, 1H), 2.81-2.68 (m, 2H), 1.90-1.83 (m, 1H), 1.45 (brs, 1H), 1.22 (d, J=6.4 Hz, 3H).

Embodiment 10

The First Step

The compound 7a (80 mg, 0.22 mmol) was dissolved in 1 mL dichloromethane, then m-chloroperbenzoic acid (68 mg, 0.33 mmol, 85%) was added into the reaction mixture at 0° C. and under the protection of nitrogen. The reaction mixture obtained was stirred at 25° C. for 4 hrs. After completion of the reaction, the reaction was quenched by adding saturated sodium carbonate aqueous solution (20 mL) and saturated sodium thiosulfate aqueous solution (20 mL) at 0° C., extracted with EtOAc (50 mL×3), the organic phases were combined and then washed by saturated brine (20 mL×3), dried over anhydrous sodium sulfate, filtered and concentrated then purified by thin layer chromatography (methanol/dichloromethane=1:10) to give the compound 9a. MS-ESI calculated value [M+H]$^+$ 376, measured value 376.

<sup>1</sup>H NMR (400 MHz, CDCl$_3$) δ 8.82 (s, 1H), 8.61 (d, J=7.6 Hz, 1H), 8.25 (d, J=7.6 Hz, 2H), 7.91 (d, J=8.4 Hz, 1H), 7.71 (t, J=8.0 Hz, 1H), 4.31-4.29 (m, 1H), 3.97 (d, J=7.2 Hz, 1H), 3.71-3.66 (m, 1H), 3.35-3.33 (m, 1H), 3.30-3.26 (m, 1H), 3.04-3.03 (m, 2H), 2.04-1.93 (m, 1H), 1.86 (s, 3H), 1.76-1.70 (m, 1H), 1.21 (d, J=6.8 Hz, 3H).

The Second Step

The compound 9a (66 mg, 0.18 mmol) was dissolved in 1 mL acetic anhydride, under the protection of nitrogen, the mixture was stirred at 120° C. for 4 hrs. After completion of the reaction, the reaction mixture was concentrated, then quenched by saturated sodium carbonate aqueous solution (20 mL) at 0° C., then extracted with EtOAc (50 mL×3), the organic phases were combined and was washed with saturated brine (20 mL×3), dried over anhydrous sodium sulfate, filtered and concentrated. The residue was purified by thin layer chromatography (methanol/dichloromethane=1:10) to give the compound 9b.

MS-ESI calculated value [M+H]$^+$ 376, measured value 376.

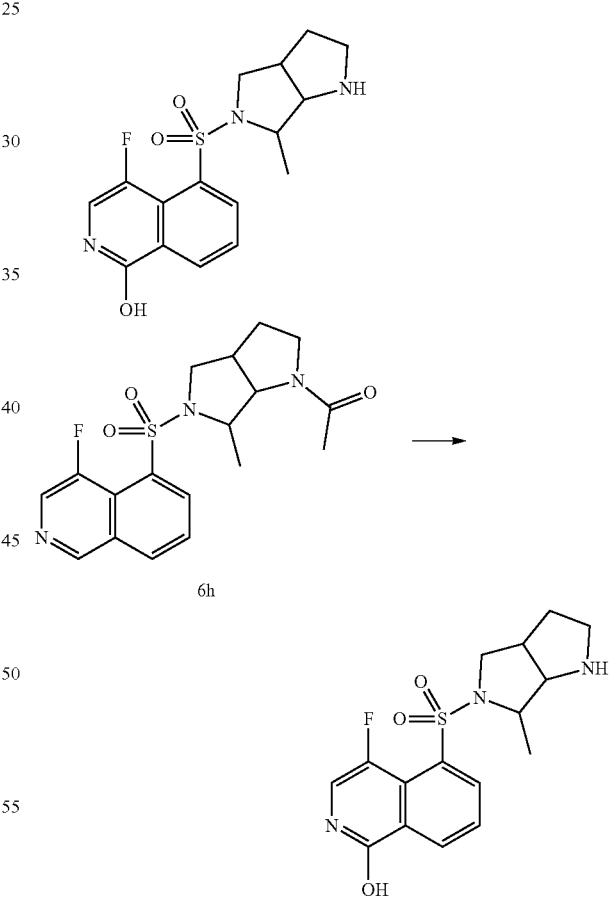

10

The First Step

The compound 10 was obtained by a three-step of reaction from the compound 6h using the synthesis method in embodiment 9.

MS-ESI calculated value [M+H]+ 352, measured value 352.

$^1$H NMR (400 MHz, CD$_3$OD) δ 8.66-8.63 (m, 2H), 7.74 (t, J=8.0 Hz, 1H), 7.45 (d, J=8.0 Hz, 1H), 4.08-4.06 (m, 1H), 3.72-3.64 (m, 2H), 3.37-3.34 (m, 1H), 3.18-3.10 (m, 1H), 3.04-3.02 (m, 2H), 2.09-2.04 (m, 1H), 1.75-1.72 (m, 1H), 1.21 (d, J=6.4 Hz, 3H).

Embodiment 11

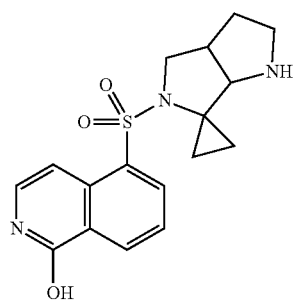

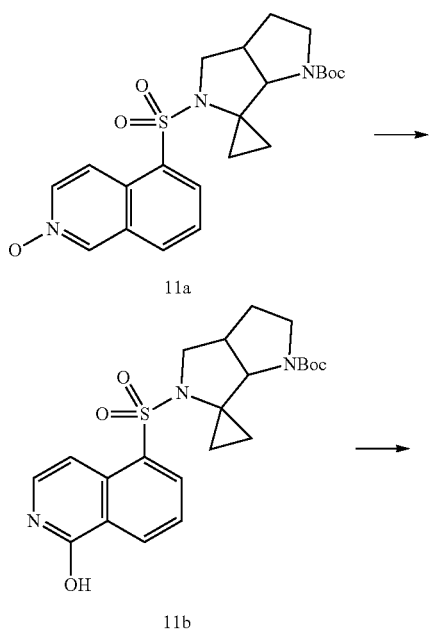

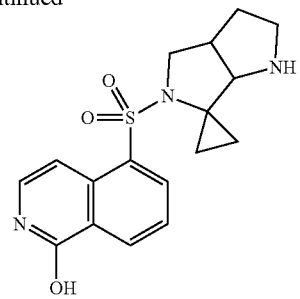

11

The First Step

The compound 11a was obtained from the compound 1j using the synthesis method in the first step of embodiment 9.

The Second Step

Benzoyl chloride (25 mg, 0.18 mmol) was added into a solution of the compound 11a (40 mg, 0.09 mmol), tetrabutylammonium bromide (6 mg, 0.02 mmol) and sodium acetate (22 mg, 0.27 mmol) in a mixed solvent of 3 mL water and 3 mL dichloromethane. The reaction mixture obtained was reacted at 20° C. for 1 hr. After completion of the reaction, the liquid was separated, while the aqueous phase was extracted with dichloromethane (5 mL×2), the organic phase was dried over anhydrous sodium sulfate, filtered and concentrated, then the crude product was purified by thin layer chromatography (EtOAc) to give the compound 11b.

The Third Step

The compound 11 was obtained from the compound 11b (15 mg, 0.03 mmol) using the synthesis method in the eight step of embodiment 1.

MS-ESI calculated value [M+H]+ 346, measured value 346.

$^1$H NMR (400 MHz, D$_2$O) δ 8.54 (brd, J=8.0 Hz, 1H), 8.38 (brd, J=7.6 Hz, 1H), 7.65 (t, J=8.0 Hz, 1H), 7.39 (d, J=7.6 Hz, 1H), 7.14 (d, J=7.6 Hz, 1H), 4.00-3.83 (m, 2H), 3.75-3.65 (m, 1H), 3.54-3.39 (m, 1H), 3.35-3.14 (m, 2H), 2.41-2.28 (m, 1H), 2.08-1.93 (m, 1H), 1.36-1.24 (m, 1H), 1.13-0.99 (m, 1H), 0.84-0.72 (m, 1H), 0.65-0.53 (m, 1H).

Evaluation of ROCK Protein Kinase Inhibitory Activity In Vitro

Experimental object: detecting the inhibitory IC$_{50}$ value of ROCK protein kinase of the compounds.

Experimental Materials:

Assay buffer solution: 20 mM Hepes (pH 7.5), 10 mM MgCl$_2$, 1 mM EGTA, 0.02% Brij35, 0.02 mg/ml BSA, 0.1 mM Na$_3$VO$_4$, 2 mM DTT, 1% DMSO Experimental Operation:

ROCK protein kinase substrate Long S6 Kinase substrate peptide was added to the freshly prepared buffer solution at a concentration of 20 μM. Then 1 nM ROCK protein kinase was added and stirred evenly. A series of DMSO dilutions containing the test compound or positive reference (starting at 100μ, 3-fold serial dilution) was added using a Echo550. After pre-incubating at room temperature for 20 minutes, $^{33}$P-ATP (radiation intensity 10 μCi/μL) was added to initiate the reaction and the reaction was carried out at room temperature for two hours. It was then filtered using P81 ion exchange paper (Whatman #3698-915) and washed with 0.75% phosphoric acid. The Filter-Binding method was used to detect radiation intensity.

The protein kinase inhibitory activity of the compound was expressed as the residual protein kinase activity of a relatively blank substrate (DMSO alone). $IC_{50}$ values and curves were calculated using Prism software package (GraphPad Software, san Diego Calif., USA). The results are shown in Table 1.

In this experiment, Fasudil was used as a positive reference.

Experimental Results:

TABLE 1

Test results of protein kinase inhibitory activity

| Samples (compounds obtained in the embodiments) | Protein kinase inhibitory activity (nM) |
| --- | --- |
| embodiment 1 | 20 |
| embodiment 2 | 32 |
| embodiment 3 | 93 |
| embodiment 6 | 12 |
| embodiment 6-1/6-2 | 65/8 |
| embodiment 7 | 28 |
| embodiment 7-1/7-2 | 63/15 |
| embodiment 8 | 18 |
| embodiment 10 | 783 |
| Fasudil | 116 |

The results show that the compounds of the present disclosure have significant and unexpected protein kineses inhibitory activity.

Evaluation of Pharmacokinetics in Rats

Experimental Object

Male SD rats were used as test animals, after a single administration, the blood concentrations of the compounds were measured and the pharmacokinetic behavior was evaluated.

Experimental Operation

Six healthy adult male SD rats (7-10 weeks of age, purchased from Shanghai Slack Experimental Animal Co., Ltd.) were randomly divided into two groups of three animals each, and one group was administered the test compound intravenously at 2 mg/kg, the other group was administered orally by gavage the test compound at 10 mg/kg. The vehicle in the intravenous administration group and the gastric administration group was both 10% DMSO+ 18% HP-β-CD+72% physiological saline. Blood samples were collected from the animals in the intravenous group at 0.0833, 0.25, 0.5, 1, 2, 4, 8, and 24 hours after the administration, and blood samples were collected from the animals in the gavage group at 0.25, 0.5, 1, 2, 4, 6, 8 and 24 hours after the administration. LCMS-MS method was used to determine the plasma drug concentration. WinNonlin™ version 6.3 (Pharsight Mountain View, Calif.) pharmacokinetic software was used to calculate the relevant pharmacokinetic parameters by non-compartment model logarithmic trapezoid method.

Experimental Results
The test results are shown in Table 2.

TABLE

Evaluation of pharmacokinetics in rats

| | Embodiment 6 | Embodiment 38 (WO2015/165341) |
| --- | --- | --- |
| Clearance rate (Cl, mL/min/kg) | 43.8 | 153 |
| Half-life period ($T_{1/2}$, hr) | 1.12 | 0.48 |

The results show that the half-life of the compound of the present disclosure was increased by about 3 times, and the clearance rate was significantly reduced, which proves that the present disclosure has more superior properties than the prior art.

Pharmacodynamics in Rats

Experimental Object

To investigate the effect of the test compound (Embodiment 6) on unilateral pulmonary fibers in the left lung of SD rats, with reference to fasudil and the clinical treatment drugs pirfenidone and nintedanib, which empoly similar mechanism of action.

Experimental Operation

Male SD rats were randomly divided into eleven groups based on body weight, namely the sham-operated group, the model group, the nintedanib 100 and 30 mg/kg/d-qd group, the pirfenidone 50 and 15 mg/kg/d-bid group, fasudil 25 mg/kg/d-qd group, test compound (Embodiment 6) 1, 3, 10 mg/kg/d-bid group and test compound (Embodiment 6) 3 mg/kg/d-qd group. Animals in each group started to be administered orally by gavage on the $8^{th}$ day of modeling for a total of 14 days. All animals were euthanized the next day after the last administration, and the left lung was taken, and the same amount of formalin solution was infused into the lungs, the lung fibrosis score was analyzed by weighing and lung pathology.

Experimental Results

Masson Trichrome staining was used for pathological evaluation of pulmonary fibrosis lesion area, pulmonary fibrosis pathology score, and fibrosis grade parameters for left lung pulmonary fibrosis lesions. Pulmonary fibrosis ashcraft score results showed that the positive drugs nintedaniband pirfenidone significantly improved the degree of pulmonary fibrosis compared with the model group ($p<0.05$) (FIG. 1), the test compound (embodiment 6) was orally administered twice a day at three different doses for 14 consecutive days, showing significant inhibition of pulmonary fibrosis, which was significantly different from the model group ($p<0.001$) (FIG. 1), but no clear dose-dependent efficacy response was observed. The test compound (embodiment 6) was administrated orally once a day at 3 mg/kg also showed a significant effect on inhibiting pulmonary fibrosis, which was consistent with the effect of twice daily oral administration of the same dose, and no significant difference was observed (FIG. 1). The test compound fasudil was administered orally once a day at 25 mg/kg for 14 consecutive days and achieved the same effect as the positive drug in inhibiting pulmonary fibrosis ($p<0.001$) (FIG. 1). The percentage of pulmonary fibrosis was calculated based on ashcraft score, with a boundary line of the score of 3, for the score below 3 (including 3), or above 4 (including 4), the result showed that 65% or more of the lesion area had a score of 4 or more than 4, after drug therapy, more than 70% of the lesion area of the animals in each drug therapy group scored below 3. The statistical results showed that the positive drugs nintedanib and pirfenidone had significant differences compared with the model group ($p<0.001$); the test compound (Embodiment 6) had a significant statistical difference compared with the model group and different doses treatment groups, but no significant dose-dependent effect was observed. (FIG. 2).

Experimental conclusion: In the bleomycin-induced rat pulmonary fibrosis model, the test compound (Embodiment 6) was administered continuously for two weeks and showed a dose-dependent effect on inhibiting pulmonary fibrosis, and it was effective at as low as 1 mg/kg BID. The test compound (Embodiment 6) could achieve a pulmonary fibrosis-improving effect comparable to that of nintedanib, pirfenidone, and fasudil at lower doses.

hERG Experiment

The cells stably expressing hERG potassium channel used in the experiment were derived from CHO-hERE of Aviva Biosciences, CHO-hERG was cultured under 5% $CO_2$ at 37° C. hERGQPatch$^{HTX}$ experiments were performed at room temperature. QPatch AssaySoftware 5.2 (Sophion Bioscience) software was used to establish whole-cell protocols, voltage stimulation protocols and compound detection protocols. First, the voltage stimulation was repeated for 30 times, this section was used as the baseline area for subsequent analysis, then 5 μL extracellular fluid was added and repeated three times. The effect concentrations of each compound were added one after the other, repeating three times by the addition of 5 μL volume. The cells were incubated at each test concentration for at least 5 mins. During the entire recording process, each indicator must meet the data analysis acceptance criteria, if the criterion is not met, the cell will not be counted in the analysis range, and the compound will be tested again, the above recording process is automatically operated by Qpatch analysis software. Each compound was tested at a concentration of 0.24 μM, 1.2004, 6.00 μM, and 30.00 μM, each concentration was repeated for at least two cells. In each complete current record, based on the percentage of peak current in the negative control group, the percentage inhibition of the effect concentration of each compound can be calculated. The standard Greek equation is used to fit the dose-response curve, and the specific equation is as follows:

$$I_{(C)} = I_b + (I_f - I_b) * c^n / (IC_{50}^n + c^n)$$

C is the test concentration of the compound, n is the slope.

The curve fitting and inhibition rate calculations were completed by Qpatch analysis software, if the inhibition rate exceeds the half inhibition at the lowest concentration or the inhibition rate does not reach the half inhibition at the highest concentration, then the corresponding $IC_{50}$ of the compound is lower than the lowest concentration or the $IC_{50}$ value is greater than the highest concentration.

Experimental Results

The results of hERG inhibitory activity of compounds of the Embodiments are shown in Table 3.

TABLE 3

| Evaluation of hERG inhibitory activity | | |
|---|---|---|
|  | Embodiment 6 | Embodiment 38 (WO2015/165341) |
| hERG (μM) | >30 | 4.6 |

The results show that the compounds of the present disclosure have a lower potential risk for hERG than the prior art.

What is claimed is:

1. A compound represented by formula (I):

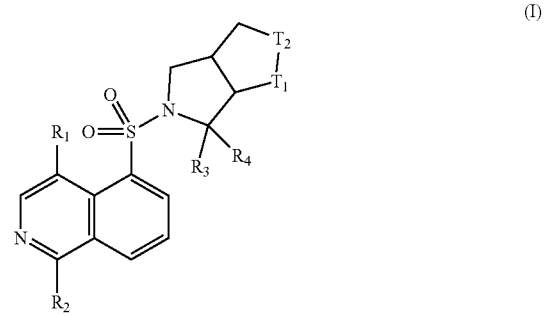

or a pharmaceutically acceptable salt, stereoisomer, or tautomer thereof, wherein:

$R_1$ is H, F, Cl, Br, I, $C_{1-3}$ alkyl, $NH_2$, or OH, wherein the $C_{1-3}$ alkyl is optionally substituted by 1, 2, or 3 independently selected R substituents;

$R_2$ is H, F, Cl, Br, I, $NH_2$, or OH;

$R_3$ and $R_4$, together with the carbon atom to which they are attached, form a 3-membered ring, wherein the 3-membered ring is optionally substituted by 1, 2, or 3 independently selected R substituents;

each R is independently F, Cl, Br, I, $NH_2$, or OH;

$T_1$ is —$CH_2$— or —NH—; and $T_2$ is —$CH_2$— or —NH—.

2. The compound of claim 1, or a pharmaceutically acceptable salt, stereoisomer, or tautomer thereof, wherein:

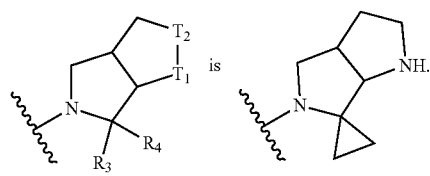

3. A compound selected from the group consisting of:

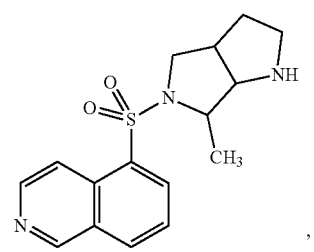

,

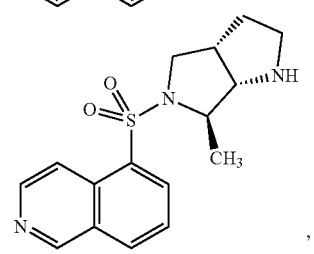

,

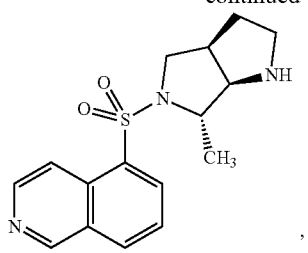
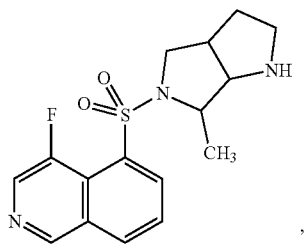
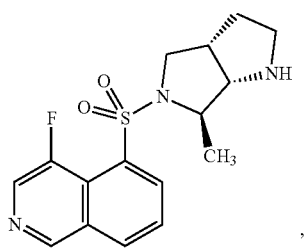
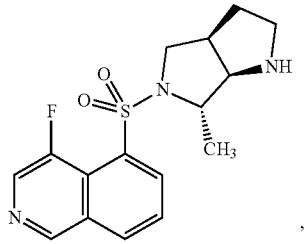
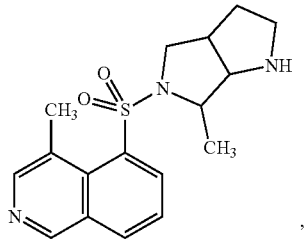
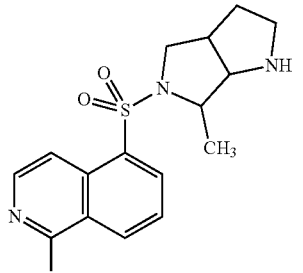
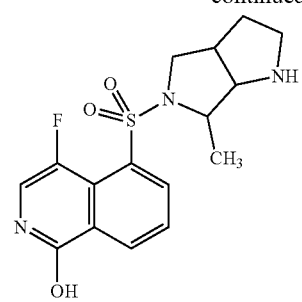
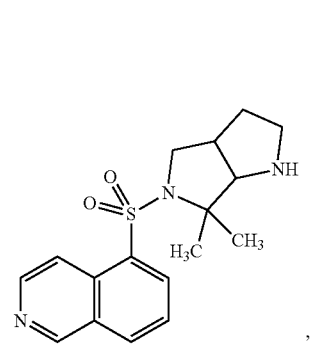
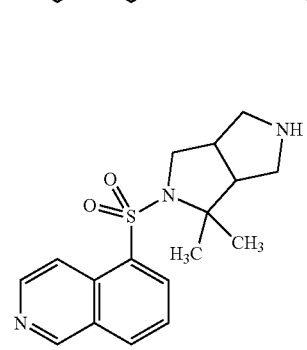
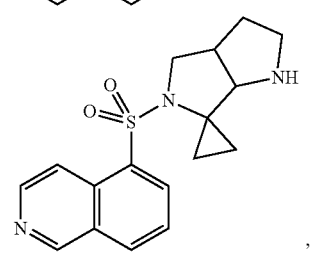
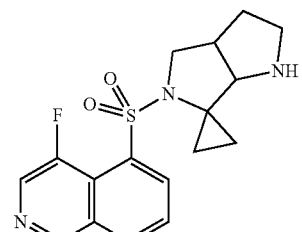
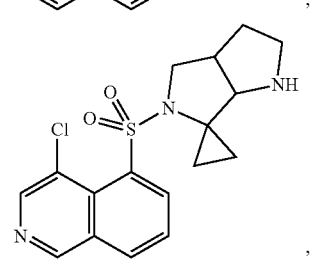
, and -continued

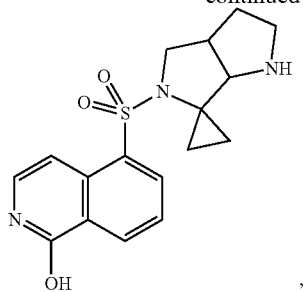

or a pharmaceutically acceptable salt or tautomer thereof.

4. A method for inhibiting rho-associated protein kinase activity in a subject in need thereof, wherein the method comprises administering to the subject a therapeutically effective amount of a compound represented by formula (I):

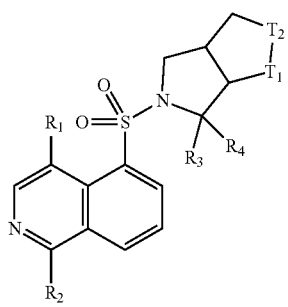

or a pharmaceutically acceptable salt, stereoisomer, or tautomer thereof,
wherein:
- $R_1$ is H, F, Cl, Br, I, $C_{1-3}$ alkyl, $NH_2$, or OH, wherein the $C_{1-3}$ alkyl is optionally substituted by 1, 2, or 3 independently selected R substituents;
- $R_2$ is H, F, Cl, Br, I, $NH_2$, or OH;
- $R_3$ is H, F, Cl, Br, I, $C_{1-3}$ alkyl, $NH_2$, or OH, wherein the $C_{1-3}$ alkyl is optionally substituted by 1, 2, or 3 independently selected R substituents;
- $R_4$ is $C_{1-3}$ alkyl, wherein the $C_{1-3}$ alkyl is optionally substituted by 1, 2, or 3 independently selected R substituents; or
- $R_3$ and $R_4$, together with the carbon atom to which they are attached, form a 3- to 6-membered ring, wherein the 3- to 6-membered ring is optionally substituted by 1, 2, or 3 independently selected R substituents;
- each R is independently F, Cl, Br, I, $NH_2$, or OH;
- $T_1$ is —$CH_2$— or —NH—; and
- $T_2$ is —$CH_2$— or —NH—.

5. The method of claim 4, wherein the subject has a disease or disorder caused by vasoconstriction selected from the group consisting of angina, cerebral angiospasm caused by subarachnoid hemorrhage, cerebral embolism, cerebral injury, cerebral ischemia, fibrosis, glaucoma, hypertension, and vertebrobasilar insufficiency.

6. A method for inhibiting rho-associated protein kinase activity in a subject in need thereof, wherein the method comprises administering to the subject a therapeutically effective amount of a pharmaceutical composition comprising a pharmaceutically acceptable carrier and as an active ingredient a compound represented by formula (I):

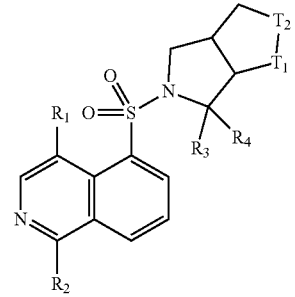

or a pharmaceutically acceptable salt, stereoisomer, or tautomer thereof,
wherein:
- $R_1$ is H, F, Cl, Br, I, $C_{1-3}$ alkyl, $NH_2$, or OH, wherein the $C_{1-3}$ alkyl is optionally substituted by 1, 2, or 3 independently selected R substituents;
- $R_2$ is H, F, Cl, Br, I, $NH_2$, or OH;
- $R_3$ is H, F, Cl, Br, I, $C_{1-3}$ alkyl, $NH_2$, or OH, wherein the $C_{1-3}$ alkyl is optionally substituted by 1, 2, or 3 independently selected R substituents;
- $R_4$ is $C_{1-3}$ alkyl, wherein the $C_{1-3}$ alkyl is optionally substituted by 1, 2, or 3 independently selected R substituents; or
- $R_3$ and $R_4$, together with the carbon atom to which they are attached, form a 3- to 6-membered ring, wherein the 3- to 6-membered ring is optionally substituted by 1, 2, or 3 independently selected R substituents;
- each R is independently F, Cl, Br, I, $NH_2$, or OH;
- $T_1$ is —$CH_2$— or —NH—; and
- $T_2$ is —$CH_2$— or —NH—.

7. The method of claim 6, wherein the subject has a disease or disorder caused by vasoconstriction selected from the group consisting of angina, cerebral angiospasm caused by subarachnoid hemorrhage, cerebral embolism, cerebral injury, cerebral ischemia, fibrosis, glaucoma, hypertension, and vertebrobasilar insufficiency.

8. A method for inhibiting human Ether-à-go-go-Related Gene potassium channel activity in a subject in need thereof, wherein the method comprises administering to the subject a therapeutically effective amount of a compound represented by formula (I):

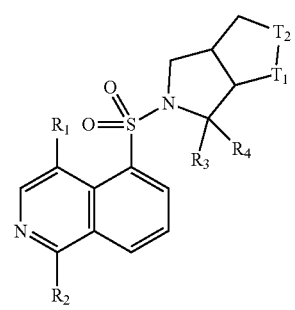

or a pharmaceutically acceptable salt, stereoisomer, or tautomer thereof, wherein:

$R_1$ is H, F, Cl, Br, I, $C_{1-3}$ alkyl, $NH_2$, or OH, wherein the $C_{1-3}$ alkyl is optionally substituted by 1, 2, or 3 independently selected R substituents;

$R_2$ is H, F, Cl, Br, I, $NH_2$, or OH;

$R_3$ is H, F, Cl, Br, I, $C_{1-3}$ alkyl, $NH_2$, or OH, wherein the $C_{1-3}$ alkyl is optionally substituted by 1, 2, or 3 independently selected R substituents;

$R_4$ is $C_{1-3}$ alkyl, wherein the $C_{1-3}$ alkyl is optionally substituted by 1, 2, or 3 independently selected R substituents; or $R_3$ and $R_4$, together with the carbon atom to which they are attached, form a 3- to 6-membered ring, wherein the 3- to 6-membered ring is optionally substituted by 1, 2, or 3 independently selected R substituents;

each R is independently F, Cl, Br, I, $NH_2$, or OH;

$T_1$ is —$CH_2$— or —NH—; and $T_2$ is —$CH_2$— or —NH—.

9. The method of claim 8, wherein the subject has a disease or disorder caused by vasoconstriction selected from the group consisting of angina, cerebral angiospasm caused by subarachnoid hemorrhage, cerebral embolism, cerebral injury, cerebral ischemia, fibrosis, glaucoma, hypertension, and vertebrobasilar insufficiency.

10. A method for inhibiting human Ether-à-go-go-Related Gene potassium channel activity in a subject in need thereof, wherein the method comprises administering to the subject a therapeutically effective amount of a pharmaceutical composition comprising a pharmaceutically acceptable carrier and as an active ingredient a compound represented by formula (I):

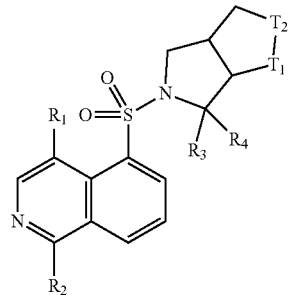

(I)

or a pharmaceutically acceptable salt, stereoisomer, or tautomer thereof, wherein:

$R_1$ is H, F, Cl, Br, I, $C_{1-3}$ alkyl, $NH_2$, or OH, wherein the $C_{1-3}$ alkyl is optionally substituted by 1, 2, or 3 independently selected R substituents;

$R_2$ is H, F, Cl, Br, I, $NH_2$, or OH;

$R_3$ is H, F, Cl, Br, I, $C_{1-3}$ alkyl, $NH_2$, or OH, wherein the $C_{1-3}$ alkyl is optionally substituted by 1, 2, or 3 independently selected R substituents;

$R_4$ is $C_{1-3}$ alkyl, wherein the $C_{1-3}$ alkyl is optionally substituted by 1, 2, or 3 independently selected R substituents; or $R_3$ and $R_4$, together with the carbon atom to which they are attached, form a 3- to 6-membered ring, wherein the 3- to 6-membered ring is optionally substituted by 1, 2, or 3 independently selected R substituents;

each R is independently F, Cl, Br, I, $NH_2$, or OH;

$T_1$ is —$CH_2$— or —NH—; and $T_2$ is —$CH_2$— or —NH—.

11. The method of claim 10, wherein the subject has a disease or disorder caused by vasoconstriction selected from the group consisting of angina, cerebral angiospasm caused by subarachnoid hemorrhage, cerebral embolism, cerebral injury, cerebral ischemia, fibrosis, glaucoma, hypertension, and vertebrobasilar insufficiency.

* * * * *